(12) United States Patent
Metzger et al.

(10) Patent No.: US 7,445,639 B2
(45) Date of Patent: *Nov. 4, 2008

(54) KNEE JOINT PROSTHESIS

(75) Inventors: Robert G Metzger, Wakarusa, IN (US); Jacy C Hoeppner, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 88 days.

This patent is subject to a terminal disclaimer.

(21) Appl. No.: 11/358,926

(22) Filed: Feb. 21, 2006

(65) Prior Publication Data

US 2006/0142867 A1 Jun. 29, 2006

Related U.S. Application Data

(60) Division of application No. 10/289,585, filed on Nov. 7, 2002, now Pat. No. 7,025,788, which is a continuation-in-part of application No. 09/792,172, filed on Feb. 23, 2001, now abandoned.

(51) Int. Cl.
*A61F 2/38* (2006.01)
*A61F 2/30* (2006.01)

(52) U.S. Cl. .................................. 623/20.15

(58) Field of Classification Search ............ 623/20.11, 623/20.14, 20.15, 20.21, 20.28–20.36, 23.18, 623/23.26, 23.34, 23.35, 23.44–23.46, 21.11, 623/21.12, 21.15, 21.18, 21.19, 22.11, 22.4, 623/22.42, 23.39, 23.47

See application file for complete search history.

(56) References Cited

U.S. PATENT DOCUMENTS

| | | | |
|---|---|---|---|
| 3,806,961 A | 4/1974 | Muller et al. | |
| 3,848,272 A | 11/1974 | Noiles | |
| 3,859,992 A | 1/1975 | Amstutz | |
| 3,878,566 A | 4/1975 | Bechtol | |
| 3,964,106 A | 6/1976 | Hutter, Jr. et al. | |
| 4,001,897 A | 1/1977 | Rambert et al. | |
| 4,007,495 A | 2/1977 | Frazier | |

(Continued)

FOREIGN PATENT DOCUMENTS

DE 3336004 A1 * 6/1985

(Continued)

OTHER PUBLICATIONS

European Search Report for EP 02 25 1274 completed on Sep. 12, 2003 (mailed on Sep. 22, 2003).

(Continued)

*Primary Examiner*—David J. Isabella
*Assistant Examiner*—Javier G Blanco
(74) *Attorney, Agent, or Firm*—Harness, Dickey & Pierce, P.L.C.

(57) ABSTRACT

A modular component for a knee joint prosthesis is disclosed. The modular component includes a tray, a stem and an adapter assembly. The tray includes a support surface and downwardly extending extension having a generally circular shape. The stem includes a main body portion and an upwardly extending extension. The adapter assembly connects the tray and the stem. The adapter assembly includes a first generally cylindrical cavity receiving the downwardly extending extension of the tray and a second generally cylindrical cavity receiving the upwardly extension of the stem.

13 Claims, 9 Drawing Sheets

U.S. PATENT DOCUMENTS

| | | |
|---|---|---|
| 4,012,796 A | 3/1977 | Weisman et al. |
| 4,041,550 A | 8/1977 | Frazier |
| 4,151,615 A | 5/1979 | Hall |
| 4,202,055 A | 5/1980 | Reiner et al. |
| 4,224,698 A | 9/1980 | Hopson |
| 4,284,080 A | 8/1981 | Rehder et al. |
| 4,305,394 A | 12/1981 | Bertuch, Jr. |
| 4,344,192 A | 8/1982 | Imbert et al. |
| 4,404,691 A | 9/1983 | Buning et al. |
| 4,475,549 A | 10/1984 | Oh |
| RE31,865 E | 4/1985 | Roux et al. |
| 4,549,319 A | 10/1985 | Meyer |
| 4,579,558 A | 4/1986 | Ramer |
| 4,619,658 A | 10/1986 | Pappas et al. |
| 4,624,674 A | 11/1986 | Pappas et al. |
| 4,632,111 A | 12/1986 | Roche |
| 4,655,777 A | 4/1987 | Dunn et al. |
| 4,661,112 A | 4/1987 | Muller et al. |
| 4,676,797 A | 6/1987 | Anapliotis et al. |
| 4,676,798 A | 6/1987 | Noiles |
| 4,676,799 A | 6/1987 | Legrand et al. |
| 4,698,063 A | 10/1987 | Link et al. |
| 4,711,233 A | 12/1987 | Brown |
| 4,714,477 A | 12/1987 | Fichera et al. |
| 4,716,894 A | 1/1988 | Lazzeri et al. |
| 4,718,911 A | 1/1988 | Kenna |
| 4,718,915 A | 1/1988 | Epinette et al. |
| 4,718,916 A | 1/1988 | Morscher et al. |
| 4,728,333 A | 3/1988 | Masse et al. |
| 4,737,411 A | 4/1988 | Graves, Jr. et al. |
| 4,764,171 A | 8/1988 | Harder et al. |
| 4,770,658 A | 9/1988 | Geremakis |
| 4,770,659 A | 9/1988 | Kendall |
| 4,770,660 A | 9/1988 | Averill |
| 4,770,661 A | 9/1988 | Oh |
| 4,778,474 A | 10/1988 | Homsy |
| 4,784,662 A | 11/1988 | Muller et al. |
| 4,784,663 A | 11/1988 | Kenna |
| 4,790,852 A | 12/1988 | Noiles |
| 4,790,854 A | 12/1988 | Harder et al. |
| 4,795,470 A | 1/1989 | Goymann et al. |
| 4,795,471 A | 1/1989 | Oh |
| 4,798,610 A | 1/1989 | Averill et al. |
| 4,801,301 A | 1/1989 | Noiles |
| 4,813,961 A | 3/1989 | Sostegni et al. |
| 4,822,366 A | 4/1989 | Bolesky |
| 4,827,919 A | 5/1989 | Barbarito et al. |
| 4,828,566 A | 5/1989 | Griss et al. |
| 4,842,606 A | 6/1989 | Kranz et al. |
| 4,846,840 A | 7/1989 | Leclercq et al. |
| 4,851,007 A | 7/1989 | Gray |
| 4,871,368 A | 10/1989 | Wagner et al. |
| 4,878,916 A | 11/1989 | Rhenter et al. |
| 4,883,492 A | 11/1989 | Frey et al. |
| 4,888,021 A | 12/1989 | Forte et al. |
| 4,904,265 A | 2/1990 | MacCollum et al. |
| 4,908,033 A | 3/1990 | Frey et al. |
| 4,908,034 A | 3/1990 | Weightman et al. |
| 4,908,036 A | 3/1990 | Link et al. |
| 4,911,723 A | 3/1990 | Menschik et al. |
| 4,919,674 A | 4/1990 | Schelhas et al. |
| 4,923,472 A | 5/1990 | Ugolini et al. |
| 4,936,853 A | 6/1990 | Fabian et al. |
| 4,936,855 A | 6/1990 | Sherman |
| 4,936,861 A | 6/1990 | Muller et al. |
| 4,938,769 A | 7/1990 | Shaw |
| 4,938,772 A | 7/1990 | Frey et al. |
| 4,944,756 A | 7/1990 | Kenna |
| 4,944,757 A | 7/1990 | Martinez et al. |
| 4,950,297 A | 8/1990 | Elloy et al. |
| 4,950,298 A | 8/1990 | Gustilo et al. |
| 4,950,299 A | 8/1990 | Noiles |
| 4,960,427 A | 10/1990 | Noiles |
| 4,961,748 A | 10/1990 | Frey et al. |
| 4,963,154 A | 10/1990 | Anapliotis et al. |
| 4,963,155 A | 10/1990 | Lazzeri et al. |
| 4,964,869 A | 10/1990 | Auclair et al. |
| 4,978,356 A | 12/1990 | Noiles |
| 4,985,037 A | 1/1991 | Petersen |
| 4,990,161 A | 2/1991 | Kampner |
| 4,994,064 A | 2/1991 | Aboczky |
| 4,995,883 A | 2/1991 | Demane et al. |
| 5,002,578 A | 3/1991 | Luman |
| 5,002,581 A | 3/1991 | Paxson et al. |
| 5,009,666 A | 4/1991 | Van Syckle et al. |
| 5,019,103 A | 5/1991 | Van Zile et al. |
| 5,019,105 A | 5/1991 | Wiley |
| 5,019,108 A | 5/1991 | Bertin et al. |
| 5,021,062 A | 6/1991 | Adrey et al. |
| 5,030,221 A | 7/1991 | Buechel et al. |
| 5,037,424 A | 8/1991 | Aboczsky |
| 5,037,438 A | 8/1991 | Davidson |
| 5,037,441 A | 8/1991 | Bouvet et al. |
| 5,041,140 A | 8/1991 | Teinturier et al. |
| 5,061,269 A | 10/1991 | Muller |
| 5,061,270 A | 10/1991 | Aboczky |
| 5,062,853 A | 11/1991 | Forte |
| 5,074,879 A | 12/1991 | Pappas et al. |
| 5,080,677 A | 1/1992 | Shelley et al. |
| 5,084,051 A | 1/1992 | Tormala et al. |
| 5,092,900 A | 3/1992 | Marchetti et al. |
| 5,098,437 A | 3/1992 | Kashuba et al. |
| 5,108,437 A | 4/1992 | Kenna |
| 5,108,439 A | 4/1992 | Morscher et al. |
| 5,108,445 A | 4/1992 | Ashby et al. |
| 5,108,446 A | 4/1992 | Wagner et al. |
| 5,108,450 A | 4/1992 | Horber et al. |
| 5,112,338 A | 5/1992 | Anspach, III |
| 5,116,339 A | 5/1992 | Glock |
| 5,116,378 A | 5/1992 | Carbone |
| 5,116,379 A | 5/1992 | McLardy-Smith et al. |
| 5,116,380 A | 5/1992 | Hewka et al. |
| 5,133,760 A | 7/1992 | Petersen et al. |
| 5,133,763 A | 7/1992 | Mullers et al. |
| 5,137,535 A | 8/1992 | Keller |
| 5,137,536 A | 8/1992 | Koshino et al. |
| 5,141,512 A | 8/1992 | Farmer et al. |
| 5,147,406 A | 9/1992 | Houston et al. |
| 5,152,796 A | 10/1992 | Slamin |
| 5,152,797 A | 10/1992 | Luckman et al. |
| 5,163,963 A | 11/1992 | Hewka et al. |
| 5,169,399 A | 12/1992 | Ryland et al. |
| 5,171,243 A | 12/1992 | Kashuba et al. |
| 5,171,276 A | 12/1992 | Caspari et al. |
| 5,171,286 A | 12/1992 | Lawes et al. |
| 5,171,313 A | 12/1992 | Salyer |
| 5,171,323 A | 12/1992 | Willert et al. |
| 5,176,709 A | 1/1993 | Branemark et al. |
| 5,180,394 A | 1/1993 | Davidson |
| 5,181,925 A | 1/1993 | Houston et al. |
| 5,181,929 A | 1/1993 | Prats et al. |
| 5,192,331 A | 3/1993 | Spotorno et al. |
| 5,194,066 A | 3/1993 | Van Zile |
| 5,197,987 A | 3/1993 | Koch et al. |
| 5,197,988 A | 3/1993 | Spotorno et al. |
| 5,201,769 A | 4/1993 | Schutzer |
| 5,211,664 A | 5/1993 | Tepic et al. |
| 5,211,666 A | 5/1993 | Fetto |
| 5,217,496 A | 6/1993 | Bruce et al. |
| 5,217,498 A | 6/1993 | Henssge et al. |
| 5,219,362 A | 6/1993 | Tuke et al. |
| 5,222,983 A | 6/1993 | Schmitz et al. |
| 5,222,984 A | 6/1993 | Forte |
| 5,226,915 A | 7/1993 | Bertin |

| | | | | | |
|---|---|---|---|---|---|
| 5,242,445 A | 9/1993 | Ashman | 5,534,032 A | 7/1996 | Hodorek |
| 5,250,051 A | 10/1993 | Maryan | 5,540,697 A | 7/1996 | Rehmann et al. |
| 5,258,034 A | 11/1993 | Furlong et al. | 5,549,684 A | 8/1996 | Amino et al. |
| 5,258,035 A | 11/1993 | Hofmann et al. | 5,549,685 A | 8/1996 | Hayes |
| 5,263,988 A | 11/1993 | Huebner | 5,549,696 A | 8/1996 | Willi et al. |
| 5,275,601 A | 1/1994 | Gogolewski et al. | 5,549,699 A | 8/1996 | MacMahon et al. |
| 5,282,867 A | 2/1994 | Mikhail | 5,549,701 A | 8/1996 | Mikhail |
| 5,282,870 A | 2/1994 | Moser et al. | 5,549,703 A | 8/1996 | Daigle et al. |
| 5,284,483 A | 2/1994 | Johnson et al. | 5,549,704 A | 8/1996 | Sutter et al. |
| 5,290,311 A | 3/1994 | Baumann et al. | 5,549,706 A | 8/1996 | McCarthy |
| 5,290,313 A | 3/1994 | Heldreth | 5,552,454 A | 9/1996 | Kretschmann et al. |
| 5,290,315 A | 3/1994 | DeCarlo, Jr. | 5,556,432 A | 9/1996 | Kubein-Meesenburg et al. |
| 5,290,318 A | 3/1994 | Ling et al. | 5,556,433 A | 9/1996 | Gabriel et al. |
| 5,292,322 A | 3/1994 | Faccioli et al. | 5,571,111 A | 11/1996 | Aboczky |
| 5,314,478 A | 5/1994 | Oka et al. | 5,571,193 A | 11/1996 | Kampner |
| 5,314,479 A | 5/1994 | Rockwood, Jr. et al. | 5,571,194 A | 11/1996 | Gabriel |
| 5,314,491 A | 5/1994 | Thongpreda et al. | 5,571,196 A | 11/1996 | Stein |
| 5,318,571 A | 6/1994 | Benson | 5,571,201 A | 11/1996 | Averill et al. |
| 5,320,625 A | 6/1994 | Bertin | 5,571,202 A | 11/1996 | Mathys, Sr. et al. |
| 5,326,358 A | 7/1994 | Aubriot et al. | 5,580,352 A | 12/1996 | Sekel et al. |
| 5,326,359 A | 7/1994 | Oudard et al. | 5,584,837 A | 12/1996 | Petersen |
| 5,330,534 A | 7/1994 | Herrington et al. | 5,593,447 A | 1/1997 | Angeli et al. |
| 5,336,267 A | 8/1994 | Kubein-Meesenburg et al. | 5,593,449 A | 1/1997 | Roberson, Jr. |
| 5,342,360 A | 8/1994 | Faccioli et al. | 5,593,450 A | 1/1997 | Scott et al. |
| 5,343,877 A | 9/1994 | Park | 5,593,451 A | 1/1997 | Averill et al. |
| 5,344,460 A | 9/1994 | Turanyi et al. | 5,609,641 A | 3/1997 | Johnson et al. |
| 5,358,529 A | 10/1994 | Davidson | 5,609,642 A | 3/1997 | Johnson et al. |
| 5,360,449 A | 11/1994 | Branemark et al. | 5,609,645 A | 3/1997 | Vinciguerra |
| 5,360,451 A | 11/1994 | Keller et al. | 5,609,647 A | 3/1997 | Kalberer et al. |
| 5,364,403 A | 11/1994 | Petersen et al. | 5,609,648 A | 3/1997 | Oehy et al. |
| 5,370,698 A | 12/1994 | Heimke et al. | 5,639,280 A | 6/1997 | Warner et al. |
| 5,370,702 A | 12/1994 | Jones | 5,641,323 A | 6/1997 | Caldarise |
| 5,376,122 A | 12/1994 | Pappas et al. | 5,645,593 A | 7/1997 | Woods et al. |
| 5,376,123 A | 12/1994 | Klaue et al. | 5,645,594 A | 7/1997 | Devanathan et al. |
| 5,376,124 A | 12/1994 | Gustke et al. | 5,645,604 A | 7/1997 | Schneider et al. |
| 5,383,938 A | 1/1995 | Rohr et al. | 5,653,765 A | 8/1997 | McTighe et al. |
| 5,387,239 A | 2/1995 | Bianco et al. | 5,658,294 A | 8/1997 | Sederholm |
| 5,387,241 A | 2/1995 | Hayes | 5,658,344 A | 8/1997 | Hurlburt |
| 5,405,392 A | 4/1995 | Deckner et al. | 5,658,346 A | 8/1997 | Willi et al. |
| 5,405,400 A | 4/1995 | Linscheid et al. | 5,658,348 A | 8/1997 | Rohr, Jr. |
| 5,405,401 A | 4/1995 | Lippincott, III et al. | 5,658,349 A | 8/1997 | Brooks et al. |
| 5,405,403 A | 4/1995 | Mikhail | 5,676,700 A | 10/1997 | Black et al. |
| 5,405,404 A | 4/1995 | Gardner et al. | 5,676,704 A | 10/1997 | Ries et al. |
| 5,413,610 A | 5/1995 | Amino et al. | 5,681,354 A | 10/1997 | Eckhoff |
| 5,417,696 A | 5/1995 | Kashuba et al. | 5,683,399 A | 11/1997 | Jones |
| 5,425,778 A | 6/1995 | Zichner et al. | 5,683,472 A | 11/1997 | O'Neil et al. |
| 5,425,779 A | 6/1995 | Schlosser et al. | 5,702,463 A | 12/1997 | Pothier et al. |
| 5,431,657 A | 7/1995 | Rohr | 5,702,475 A | 12/1997 | Zahedi et al. |
| 5,443,512 A | 8/1995 | Parr et al. | 5,702,476 A | 12/1997 | Limacher et al. |
| 5,443,516 A | 8/1995 | Albrektsson et al. | 5,702,477 A | 12/1997 | Capello et al. |
| 5,447,492 A | 9/1995 | Cartmell et al. | 5,702,478 A | 12/1997 | Tornier et al. |
| 5,458,637 A | 10/1995 | Hayes | 5,702,482 A | 12/1997 | Thongpreda et al. |
| 5,462,563 A | 10/1995 | Shearer et al. | 5,702,487 A | 12/1997 | Averill et al. |
| 5,474,560 A | 12/1995 | Rohr, Jr. | 5,725,589 A | 3/1998 | Pfaff et al. |
| 5,480,443 A | 1/1996 | Elias | 5,725,591 A | 3/1998 | DeCarlo, Jr. et al. |
| 5,480,444 A | 1/1996 | Incavo et al. | 5,725,597 A | 3/1998 | Hwang et al. |
| 5,480,445 A | 1/1996 | Burkinshaw | 5,735,901 A | 4/1998 | Maumy et al. |
| 5,480,446 A | 1/1996 | Goodfellow et al. | 5,746,771 A | 5/1998 | Clement, Jr. et al. |
| 5,480,447 A | 1/1996 | Skiba | 5,749,877 A | 5/1998 | Young et al. |
| 5,480,448 A | 1/1996 | Mikhail | 5,755,794 A | 5/1998 | Benson |
| 5,480,451 A | 1/1996 | Grundei et al. | 5,755,805 A | 5/1998 | Whiteside |
| 5,480,452 A | 1/1996 | Hofmann et al. | 5,755,806 A | 5/1998 | Stalcup et al. |
| 5,486,181 A | 1/1996 | Cohen et al. | 5,755,807 A | 5/1998 | Anstaett et al. |
| 5,489,311 A | 2/1996 | Cipolletti | 5,755,808 A | 5/1998 | DeCarlo et al. |
| 5,507,745 A | 4/1996 | Logroscino et al. | 5,766,255 A | 6/1998 | Slamin et al. |
| 5,507,817 A | 4/1996 | Craig et al. | 5,766,256 A | 6/1998 | Oudard et al. |
| 5,507,820 A | 4/1996 | Pappas | 5,766,260 A | 6/1998 | Whiteside |
| 5,507,826 A | 4/1996 | Besselink et al. | 5,766,262 A | 6/1998 | Mikhail |
| 5,507,829 A | 4/1996 | Thongpreda et al. | 5,776,200 A | 7/1998 | Johnson et al. |
| 5,507,832 A | 4/1996 | Michielli et al. | 5,776,201 A | 7/1998 | Colleran et al. |
| 5,522,902 A | 6/1996 | Yuan et al. | 5,776,202 A | 7/1998 | Copf et al. |
| 5,527,317 A | 6/1996 | Ashby et al. | 5,782,920 A | 7/1998 | Colleran |
| 5,531,793 A | 7/1996 | Kelman et al. | 5,782,921 A | 7/1998 | Colleran et al. |

| Patent No. | Date | Name |
|---|---|---|
| 5,782,924 A | 7/1998 | Johnson |
| 5,782,928 A | 7/1998 | Ries et al. |
| 5,782,930 A | 7/1998 | Lin et al. |
| 5,800,554 A | 9/1998 | Scholz et al. |
| 5,800,555 A | 9/1998 | Gray, III |
| 5,800,556 A | 9/1998 | Sanders et al. |
| 5,800,558 A | 9/1998 | LaHaise, Sr. |
| 5,800,560 A | 9/1998 | Draenert et al. |
| 5,817,096 A | 10/1998 | Salyer |
| 5,824,097 A | 10/1998 | Gabriel et al. |
| 5,824,107 A | 10/1998 | Tschirren et al. |
| 5,824,108 A | 10/1998 | Huebner |
| 5,830,215 A | 11/1998 | Incavo et al. |
| 5,858,020 A | 1/1999 | Johnson et al. |
| 5,865,850 A | 2/1999 | Matthews |
| 5,871,547 A | 2/1999 | Abouaf et al. |
| 5,879,387 A | 3/1999 | Jones et al. |
| 5,879,390 A | 3/1999 | Kubein-Meesenburg et al. |
| 5,879,391 A | 3/1999 | Slamin |
| 5,879,398 A | 3/1999 | Swarts et al. |
| 5,879,401 A | 3/1999 | Besemer et al. |
| 5,879,402 A | 3/1999 | Lawes et al. |
| 5,879,404 A | 3/1999 | Bateman et al. |
| 5,879,405 A | 3/1999 | Ries et al. |
| 5,879,406 A | 3/1999 | Lilley |
| 5,888,205 A | 3/1999 | Pratt et al. |
| 5,888,206 A | 3/1999 | Lob et al. |
| 5,888,211 A | 3/1999 | Sanders |
| 5,899,942 A | 5/1999 | Berman |
| 5,902,340 A | 5/1999 | White et al. |
| 5,904,688 A | 5/1999 | Gilbert et al. |
| 5,904,720 A | 5/1999 | Farrar et al. |
| 5,906,644 A | 5/1999 | Powell |
| 5,916,269 A | 6/1999 | Serbousek et al. |
| 5,916,270 A | 6/1999 | Lipman |
| 5,919,236 A | 7/1999 | Pfaff et al. |
| 5,928,286 A | 7/1999 | Ashby et al. |
| 5,928,287 A | 7/1999 | Keller et al. |
| 5,931,870 A | 8/1999 | Cuckler et al. |
| 5,935,171 A | 8/1999 | Schneider et al. |
| 5,935,175 A | 8/1999 | Ostiguy, Jr. et al. |
| 5,938,702 A | 8/1999 | Lopez et al. |
| 5,944,756 A | 8/1999 | Fischetti et al. |
| 5,944,759 A | 8/1999 | Link et al. |
| 5,951,603 A | 9/1999 | O'Neil et al. |
| 5,954,727 A | 9/1999 | Collazo |
| 5,957,979 A | 9/1999 | Beckman et al. |
| 5,961,516 A | 10/1999 | Graf et al. |
| 5,973,222 A | 10/1999 | Devanathan et al. |
| 5,976,148 A | 11/1999 | Charpenet et al. |
| 5,976,188 A | 11/1999 | Dextradeur et al. |
| 5,976,189 A | 11/1999 | Keller et al. |
| 5,977,204 A | 11/1999 | Boyan et al. |
| 5,980,574 A | 11/1999 | Takei et al. |
| 5,984,968 A | 11/1999 | Park |
| 5,984,969 A | 11/1999 | Matthews et al. |
| 5,989,293 A | 11/1999 | Cook et al. |
| 5,989,294 A | 11/1999 | Marlow et al. |
| 5,997,576 A | 12/1999 | Copf et al. |
| 5,997,577 A | 12/1999 | Herrington et al. |
| 5,997,579 A | 12/1999 | Albrektsson et al. |
| 6,004,353 A | 12/1999 | Masini |
| 6,005,018 A | 12/1999 | Cicierega et al. |
| 6,007,580 A | 12/1999 | Lehto et al. |
| 6,008,432 A | 12/1999 | Taylor |
| 6,010,533 A | 1/2000 | Pope et al. |
| 6,010,534 A | 1/2000 | O'Neil et al. |
| 6,013,103 A | 1/2000 | Kaufman et al. |
| 6,013,104 A | 1/2000 | Kampner |
| 6,015,937 A | 1/2000 | Branemark et al. |
| 6,027,505 A | 2/2000 | Peter et al. |
| 6,039,764 A | 3/2000 | Pottenger et al. |
| 6,042,611 A | 3/2000 | Noiles |
| 6,045,583 A | 4/2000 | Gross et al. |
| 6,053,945 A | 4/2000 | O'Neil et al. |
| 6,056,779 A | 5/2000 | Noyer et al. |
| 6,059,833 A | 5/2000 | Doets et al. |
| 6,063,091 A | 5/2000 | Lombardo et al. |
| 6,063,124 A | 5/2000 | Amstutz |
| 6,066,176 A | 5/2000 | Oshida |
| 6,071,311 A | 6/2000 | O'Neil et al. |
| 6,074,424 A | 6/2000 | Perrone, Jr. et al. |
| 6,074,425 A | 6/2000 | Pappas |
| 6,086,614 A | 7/2000 | Mumme |
| 6,087,553 A | 7/2000 | Cohen et al. |
| 6,090,146 A | 7/2000 | Rozow, III et al. |
| 6,093,208 A | 7/2000 | Tian et al. |
| 6,096,082 A | 8/2000 | Stegmuller et al. |
| 6,099,569 A | 8/2000 | Keller et al. |
| 6,099,571 A | 8/2000 | Knapp |
| 6,113,640 A | 9/2000 | Tormala et al. |
| 6,117,175 A | 9/2000 | Bosredon et al. |
| 6,120,543 A | 9/2000 | Kubein-Meesenburg et al. |
| 6,120,545 A | 9/2000 | Hamelijnck et al. |
| 6,126,690 A | 10/2000 | Ateshian et al. |
| 6,126,691 A | 10/2000 | Kasra et al. |
| 6,126,692 A | 10/2000 | Robie et al. |
| 6,126,693 A | 10/2000 | O'Neil et al. |
| 6,126,694 A | 10/2000 | Gray, Jr. |
| 6,126,695 A | 10/2000 | Semlitsch et al. |
| 6,129,765 A | 10/2000 | Lopez et al. |
| 6,132,468 A | 10/2000 | Mansmann |
| 6,132,469 A | 10/2000 | Schroeder |
| 6,136,033 A | 10/2000 | Suemer et al. |
| 6,136,035 A | 10/2000 | Lob et al. |
| 6,139,584 A | 10/2000 | Ochoa et al. |
| 6,146,424 A | 11/2000 | Gray, Jr. et al. |
| 6,149,687 A | 11/2000 | Gray, Jr. et al. |
| 6,152,930 A | 11/2000 | Mastrorio |
| 6,152,961 A | 11/2000 | Ostiguy, Jr. et al. |
| 6,156,070 A | 12/2000 | Incavo et al. |
| 6,162,255 A | 12/2000 | Oyola |
| 6,162,256 A | 12/2000 | Ostiguy, Jr. et al. |
| 6,165,220 A | 12/2000 | McKellop et al. |
| 6,165,222 A | 12/2000 | Hoeppner et al. |
| 6,168,600 B1 | 1/2001 | Grace et al. |
| 6,171,342 B1 | 1/2001 | O'Neil |
| 6,179,876 B1 | 1/2001 | Stamper et al. |
| 6,179,877 B1 | 1/2001 | Burke |
| 6,193,759 B1 | 2/2001 | Ro et al. |
| 6,197,032 B1 | 3/2001 | Lawes et al. |
| 6,200,324 B1 | 3/2001 | Regni, Jr. |
| 6,206,929 B1 | 3/2001 | Ochoa et al. |
| 6,214,014 B1 | 4/2001 | McGann |
| 6,214,052 B1 | 4/2001 | Burkinshaw |
| 6,214,053 B1 | 4/2001 | Ling et al. |
| 6,217,615 B1 | 4/2001 | Sioshansi et al. |
| 6,217,619 B1 | 4/2001 | Keller |
| 6,221,110 B1 | 4/2001 | Copf et al. |
| 6,224,633 B1 | 5/2001 | Kalberer et al. |
| 6,228,091 B1 | 5/2001 | Lombardo et al. |
| 6,228,121 B1 | 5/2001 | Khalili |
| 6,231,611 B1 | 5/2001 | Mosseri et al. |
| 6,235,060 B1 | 5/2001 | Kubein-Meesenburg et al. |
| 6,245,111 B1 | 6/2001 | Shaffner |
| 6,248,132 B1 | 6/2001 | Harris |
| 6,264,698 B1 | 7/2001 | Lawes et al. |
| 6,264,699 B1 | 7/2001 | Noiles et al. |
| 6,267,785 B1 | 7/2001 | Masini |
| 6,281,264 B1 | 8/2001 | Salovey et al. |
| 6,284,001 B1 | 9/2001 | Knapp |
| 6,290,726 B1 | 9/2001 | Pope et al. |
| 6,290,727 B1 | 9/2001 | Otto et al. |
| 6,293,971 B1 | 9/2001 | Nelson et al. |
| 6,296,667 B1 | 10/2001 | Johnson et al. |
| 6,302,890 B1 | 10/2001 | Leone, Jr. |

| Patent | Date | Inventor |
|---|---|---|
| 6,306,172 B1 | 10/2001 | O'Neil |
| 6,319,285 B1 | 11/2001 | Chamier et al. |
| 6,325,829 B1 | 12/2001 | Schmotzer et al. |
| 6,334,875 B1 | 1/2002 | Keller et al. |
| 6,340,370 B1 | 1/2002 | Willert et al. |
| 6,342,075 B1 | 1/2002 | MacArthur |
| 6,344,060 B1 | 2/2002 | Schmotzer et al. |
| 6,344,496 B1 | 2/2002 | Niederauer et al. |
| 6,352,559 B1 | 3/2002 | Church et al. |
| 6,358,282 B1 | 3/2002 | Wymann et al. |
| 6,361,566 B1 | 3/2002 | Al-Hafez et al. |
| 6,368,354 B2 | 4/2002 | Burstein et al. |
| 6,376,573 B1 | 4/2002 | White et al. |
| 6,379,389 B1 | 4/2002 | Koch et al. |
| 6,383,227 B1 | 5/2002 | Baroud et al. |
| 6,387,131 B1 | 5/2002 | Miehlke et al. |
| 6,413,280 B1 | 7/2002 | Feiler |
| 6,416,552 B1 | 7/2002 | Hoeppner et al. |
| 6,423,096 B1 | 7/2002 | Musset et al. |
| 6,425,921 B1 | 7/2002 | Grundei et al. |
| 6,428,578 B2 | 8/2002 | White |
| 6,432,141 B1 | 8/2002 | Stocks et al. |
| 6,436,145 B1 | 8/2002 | Miller |
| 6,436,146 B1 | 8/2002 | Hassler et al. |
| 6,447,549 B1 | 9/2002 | Taft |
| 6,447,550 B1 | 9/2002 | Hunter et al. |
| 6,451,058 B2 | 9/2002 | Tuke et al. |
| 6,468,281 B1 | 10/2002 | Badorf et al. |
| 6,475,243 B1 | 11/2002 | Sheldon et al. |
| 6,482,237 B2 | 11/2002 | Mosseri et al. |
| 6,488,713 B1 | 12/2002 | Hershberger |
| 6,488,715 B1 | 12/2002 | Pope et al. |
| 6,491,726 B2 | 12/2002 | Pappas |
| 6,494,914 B2 | 12/2002 | Brown et al. |
| 6,497,728 B2 | 12/2002 | Yong et al. |
| 6,500,208 B1 | 12/2002 | Metzger et al. |
| 6,503,281 B1 | 1/2003 | Mallory |
| 6,506,215 B1 | 1/2003 | Letot et al. |
| 6,517,583 B1 | 2/2003 | Pope et al. |
| 6,518,328 B2 | 2/2003 | Kumar |
| 6,520,995 B2 | 2/2003 | Church et al. |
| 6,524,344 B2 | 2/2003 | Yoon et al. |
| 6,524,345 B1 | 2/2003 | Valimaa et al. |
| 6,527,807 B1 | 3/2003 | O'Neil et al. |
| 6,527,808 B1 | 3/2003 | Albertorio et al. |
| 6,527,809 B1 | 3/2003 | Doursounian et al. |
| 6,527,810 B2 | 3/2003 | Johnson et al. |
| 6,537,321 B1 | 3/2003 | Horber et al. |
| 6,540,786 B2 | 4/2003 | Chibrac et al. |
| 6,558,427 B2 | 5/2003 | Leclercq et al. |
| 6,565,575 B2 | 5/2003 | Lewis |
| 6,565,606 B1 | 5/2003 | Bruce et al. |
| 6,589,248 B1 | 7/2003 | Hughes |
| 6,589,283 B1 | 7/2003 | Metzger et al. |
| 6,589,284 B1 | 7/2003 | Silberer et al. |
| 6,602,259 B1 | 8/2003 | Masini |
| 6,610,097 B2 | 8/2003 | Serbousek et al. |
| 6,613,092 B1 | 9/2003 | Kana et al. |
| 6,616,696 B1 | 9/2003 | Merchant |
| 6,620,198 B2 | 9/2003 | Burstein et al. |
| 6,623,488 B1 | 9/2003 | Leone, Jr. |
| 6,626,950 B2 | 9/2003 | Brown et al. |
| 6,629,999 B1 | 10/2003 | Serafin, Jr. |
| 6,641,617 B1 | 11/2003 | Merrill et al. |
| 6,652,533 B2 | 11/2003 | O'Neil |
| 6,652,586 B2 | 11/2003 | Hunter et al. |
| 6,652,589 B2 | 11/2003 | Schmotzer et al. |
| 6,652,590 B1 | 11/2003 | Zitnansky et al. |
| 6,660,040 B2 | 12/2003 | Chan et al. |
| 6,679,890 B2 | 1/2004 | Margulies et al. |
| 6,682,566 B2 | 1/2004 | Draenert et al. |
| 6,682,567 B1 | 1/2004 | Schroeder |
| 6,692,531 B1 | 2/2004 | Yoon et al. |
| 6,699,293 B2 | 3/2004 | White |
| 6,706,071 B1 | 3/2004 | Wolter et al. |
| 6,706,072 B2 | 3/2004 | Dwyer et al. |
| 6,712,857 B1 | 3/2004 | Roger et al. |
| 6,712,858 B1 | 3/2004 | Grundei et al. |
| 6,716,248 B2 | 4/2004 | Huene |
| 6,719,800 B2 | 4/2004 | Meyers et al. |
| 6,723,129 B2 | 4/2004 | Dwyer et al. |
| 6,726,725 B2 | 4/2004 | Hunter et al. |
| 6,743,258 B1 | 6/2004 | Keller et al. |
| 6,755,864 B1 | 6/2004 | Brack et al. |
| 6,758,864 B2 | 7/2004 | Storer et al. |
| 6,761,741 B2 | 7/2004 | Iesaka |
| 6,764,516 B2 | 7/2004 | Pappas |
| 6,770,097 B2 | 8/2004 | Leclercq et al. |
| 6,783,550 B2 | 8/2004 | MacArthur |
| 6,786,933 B2 | 9/2004 | Merrill et al. |
| 6,793,681 B1 | 9/2004 | Pope et al. |
| 6,800,670 B2 | 10/2004 | Shen et al. |
| 6,802,866 B2 | 10/2004 | Bunz et al. |
| 6,811,568 B2 | 11/2004 | Minamikawa et al. |
| 6,811,569 B1 | 11/2004 | Afriat et al. |
| 6,818,019 B2 | 11/2004 | Horber et al. |
| 6,818,020 B2 | 11/2004 | Sun et al. |
| 6,827,739 B2 | 12/2004 | Griner et al. |
| 6,827,742 B2 | 12/2004 | Hayes, Jr. et al. |
| 6,840,944 B2 | 1/2005 | Suddaby |
| 6,843,805 B2 | 1/2005 | Webb et al. |
| 6,843,806 B2 | 1/2005 | Hayes, Jr. et al. |
| 6,863,692 B2 | 3/2005 | Meulink |
| 6,866,683 B2 | 3/2005 | Gerbec et al. |
| 6,866,685 B2 | 3/2005 | Chan et al. |
| 6,869,447 B2 | 3/2005 | Lee et al. |
| 6,875,237 B2 | 4/2005 | Dye |
| 6,881,229 B2 | 4/2005 | Khandkar et al. |
| 6,887,276 B2 | 5/2005 | Gerbec et al. |
| 6,905,515 B1 | 6/2005 | Gilbertson |
| 6,908,486 B2 | 6/2005 | Lewallen |
| 6,916,340 B2 | 7/2005 | Metzger et al. |
| 6,916,341 B2 | 7/2005 | Rolston |
| 6,923,833 B2 | 8/2005 | Wasielewski |
| 6,926,738 B2 | 8/2005 | Wyss |
| 6,926,739 B1 | 8/2005 | O'Connor et al. |
| 6,926,740 B2 | 8/2005 | Lewis et al. |
| 6,944,518 B2 | 9/2005 | Roose |
| 6,953,479 B2 | 10/2005 | Carson et al. |
| 6,962,607 B2 | 11/2005 | Gundlapalli et al. |
| 6,966,932 B1 | 11/2005 | Schroeder |
| 6,969,406 B2 | 11/2005 | Tornier et al. |
| 6,972,021 B2 | 12/2005 | Raugel et al. |
| 6,981,991 B2 | 1/2006 | Ferree |
| 7,004,946 B2 | 2/2006 | Parker et al. |
| 7,022,142 B2 | 4/2006 | Johnson |
| 7,025,788 B2 | 4/2006 | Metzger et al. |
| 7,037,310 B2 | 5/2006 | Murphy |
| 7,044,974 B2 | 5/2006 | Garber et al. |
| 7,051,417 B2 | 5/2006 | Michelson |
| 7,056,577 B1 | 6/2006 | Bruce et al. |
| 7,070,622 B1 | 7/2006 | Brown et al. |
| 7,074,241 B2 | 7/2006 | McKinnon |
| 7,105,026 B2 | 9/2006 | Johnson et al. |
| 7,108,719 B2 | 9/2006 | Horber et al. |
| 7,131,995 B2 | 11/2006 | Biedermann et al. |
| 7,153,326 B1 | 12/2006 | Metzger |
| 7,156,880 B2 | 1/2007 | Evans et al. |
| 7,166,133 B2 | 1/2007 | Evans et al. |
| 7,189,263 B2 | 3/2007 | Erbe et al. |
| 7,192,448 B2 | 3/2007 | Ferree |
| 7,198,642 B2 | 4/2007 | Hazebrouck et al. |
| 2001/0014828 A1 | 8/2001 | Yoon |
| 2001/0014829 A1 | 8/2001 | Yoon |
| 2001/0016780 A1 | 8/2001 | Yong San |
| 2001/0018616 A1 | 8/2001 | Schwab |

| | | | | | | |
|---|---|---|---|---|---|---|
| 2001/0032021 A1 | 10/2001 | McKinnon | | 2003/0225458 A1 | 12/2003 | Donkers et al. |
| 2001/0037156 A1 | 11/2001 | Burstein et al. | | 2003/0229356 A1 | 12/2003 | Dye |
| 2001/0039456 A1 | 11/2001 | Boyer et al. | | 2003/0229398 A1 | 12/2003 | Iesaka |
| 2001/0039457 A1 | 11/2001 | Boyer et al. | | 2004/0002766 A1 | 1/2004 | Hunter et al. |
| 2001/0041941 A1 | 11/2001 | Boyer et al. | | 2004/0019380 A1 | 1/2004 | Baege et al. |
| 2001/0051830 A1 | 12/2001 | Tuke et al. | | 2004/0019382 A1 | 1/2004 | Amirouche et al. |
| 2002/0022889 A1 | 2/2002 | Chibrac et al. | | 2004/0019386 A1 | 1/2004 | Ferree |
| 2002/0022890 A1 | 2/2002 | Jacobsson et al. | | 2004/0024460 A1 | 2/2004 | Ferree |
| 2002/0040244 A1 | 4/2002 | Despres et al. | | 2004/0030344 A1 | 2/2004 | Dye et al. |
| 2002/0040245 A1 | 4/2002 | Lester et al. | | 2004/0030394 A1 | 2/2004 | Horber |
| 2002/0042656 A1 | 4/2002 | Hunter et al. | | 2004/0030400 A1 | 2/2004 | Horber |
| 2002/0045949 A1 | 4/2002 | Ling et al. | | 2004/0039449 A1 | 2/2004 | Tornier |
| 2002/0049500 A1 | 4/2002 | Draenert | | 2004/0039451 A1 | 2/2004 | Southworth |
| 2002/0052659 A1 | 5/2002 | Hayes et al. | | 2004/0049284 A1 | 3/2004 | German et al. |
| 2002/0059000 A1 | 5/2002 | Dwyer et al. | | 2004/0049285 A1 | 3/2004 | Haas |
| 2002/0068980 A1 | 6/2002 | Serbousek et al. | | 2004/0049286 A1 | 3/2004 | German et al. |
| 2002/0072799 A1 | 6/2002 | Despres et al. | | 2004/0054418 A1 | 3/2004 | McLean et al. |
| 2002/0082706 A1 | 6/2002 | Raugel | | 2004/0059427 A1 | 3/2004 | Serbousek et al. |
| 2002/0107577 A1 | 8/2002 | Storer et al. | | 2004/0068324 A1 | 4/2004 | Grundei |
| 2002/0116007 A1 | 8/2002 | Lewis | | 2004/0073226 A1 | 4/2004 | Cotting et al. |
| 2002/0116068 A1 | 8/2002 | McLean | | 2004/0073315 A1 | 4/2004 | Justin et al. |
| 2002/0120340 A1 | 8/2002 | Metzger et al. | | 2004/0078083 A1 | 4/2004 | Gibbs et al. |
| 2002/0120341 A1 | 8/2002 | Stumpo et al. | | 2004/0083004 A1 | 4/2004 | Wasielewski |
| 2002/0128653 A1 | 9/2002 | Haidukewych | | 2004/0098133 A1 | 5/2004 | Carignan et al. |
| 2002/0138148 A1 | 9/2002 | Hyde | | 2004/0098134 A1 | 5/2004 | Meulink |
| 2002/0138151 A1 | 9/2002 | Hubbard et al. | | 2004/0102851 A1 | 5/2004 | Saladino |
| 2002/0143402 A1 | 10/2002 | Steinberg | | 2004/0102852 A1 | 5/2004 | Johnson et al. |
| 2002/0143403 A1 | 10/2002 | Vaidyanathan et al. | | 2004/0107594 A1 | 6/2004 | Afriat |
| 2002/0151978 A1 | 10/2002 | Zacouto et al. | | 2004/0117023 A1 | 6/2004 | Gerbec et al. |
| 2002/0156536 A1 | 10/2002 | Harris et al. | | 2004/0117029 A1 | 6/2004 | Lewis et al. |
| 2002/0165615 A1 | 11/2002 | Abouaf et al. | | 2004/0122521 A1 | 6/2004 | Lee et al. |
| 2002/0173853 A1 | 11/2002 | Corl et al. | | 2004/0122524 A1 | 6/2004 | Hunter et al. |
| 2003/0009234 A1 | 1/2003 | Treacy et al. | | 2004/0143336 A1 | 7/2004 | Burkinshaw |
| 2003/0014120 A1* | 1/2003 | Carson et al. | | 2004/0143341 A1 | 7/2004 | McLean |
| 2003/0022069 A1 | 1/2003 | Karube et al. | | 2004/0147926 A1 | 7/2004 | Iversen |
| 2003/0033018 A1 | 2/2003 | Merchant | | 2004/0153063 A1 | 8/2004 | Harris |
| 2003/0040805 A1 | 2/2003 | Minamikawa | | 2004/0162619 A1 | 8/2004 | Blaylock et al. |
| 2003/0050645 A1 | 3/2003 | Parker et al. | | 2004/0162620 A1 | 8/2004 | Wyss |
| 2003/0050703 A1 | 3/2003 | Harris et al. | | 2004/0162621 A1 | 8/2004 | Crofford |
| 2003/0050705 A1 | 3/2003 | Cueille et al. | | 2004/0172137 A1 | 9/2004 | Blaylock et al. |
| 2003/0055508 A1 | 3/2003 | Metzger et al. | | 2004/0172139 A1 | 9/2004 | Dwyer et al. |
| 2003/0055509 A1 | 3/2003 | McCue et al. | | 2004/0186580 A1 | 9/2004 | Steinmann |
| 2003/0060889 A1 | 3/2003 | Tarabishy | | 2004/0186586 A1 | 9/2004 | Seyer et al. |
| 2003/0060890 A1 | 3/2003 | Tarabishy | | 2004/0193282 A1 | 9/2004 | Hanes |
| 2003/0065397 A1 | 4/2003 | Hanssen et al. | | 2004/0199257 A1 | 10/2004 | Dooney |
| 2003/0074078 A1 | 4/2003 | Doubler et al. | | 2004/0199259 A1 | 10/2004 | Pichon et al. |
| 2003/0093156 A1 | 5/2003 | Metzger et al. | | 2004/0204760 A1 | 10/2004 | Fitz et al. |
| 2003/0105529 A1 | 6/2003 | Synder et al. | | 2004/0204767 A1 | 10/2004 | Park et al. |
| 2003/0109933 A1 | 6/2003 | Weissman et al. | | 2004/0210316 A1 | 10/2004 | King et al. |
| 2003/0114934 A1 | 6/2003 | Steinberg | | 2004/0225368 A1 | 11/2004 | Plumet et al. |
| 2003/0114935 A1 | 6/2003 | Chan et al. | | 2004/0225370 A1 | 11/2004 | Cruchet et al. |
| 2003/0120346 A1 | 6/2003 | Mercinek et al. | | 2004/0225371 A1 | 11/2004 | Roger |
| 2003/0120347 A1 | 6/2003 | Steinberg | | 2004/0226343 A1 | 11/2004 | Babler et al. |
| 2003/0125810 A1 | 7/2003 | Sullivan et al. | | 2004/0236428 A1 | 11/2004 | Burkinshaw et al. |
| 2003/0130740 A1 | 7/2003 | Stocks et al. | | 2004/0243249 A1 | 12/2004 | Ishihara et al. |
| 2003/0139818 A1 | 7/2003 | Rogers et al. | | 2004/0255749 A1 | 12/2004 | Hayden |
| 2003/0149485 A1 | 8/2003 | Tornier | | 2004/0260396 A1 | 12/2004 | Ferree et al. |
| 2003/0153981 A1 | 8/2003 | Wang et al. | | 2004/0267374 A1 | 12/2004 | Friedrichs |
| 2003/0153982 A1 | 8/2003 | Pria | | 2004/0267375 A1 | 12/2004 | Friedrichs |
| 2003/0158606 A1 | 8/2003 | Coon et al. | | 2005/0004677 A1 | 1/2005 | Johnson |
| 2003/0163202 A1 | 8/2003 | Lakin | | 2005/0004678 A1 | 1/2005 | Richards |
| 2003/0171815 A1 | 9/2003 | Kana et al. | | 2005/0010288 A1 | 1/2005 | Merrill et al. |
| 2003/0171817 A1 | 9/2003 | Rambert et al. | | 2005/0010303 A1 | 1/2005 | Nogier |
| 2003/0181984 A1 | 9/2003 | Abendschein | | 2005/0010304 A1 | 1/2005 | Jamali |
| 2003/0181987 A1 | 9/2003 | Muirhead-Allwood | | 2005/0021149 A1 | 1/2005 | Borruto et al. |
| 2003/0204262 A1 | 10/2003 | Ferguson et al. | | 2005/0027302 A1 | 2/2005 | Cueille et al. |
| 2003/0204263 A1 | 10/2003 | Justin et al. | | 2005/0033442 A1 | 2/2005 | Fisher et al. |
| 2003/0204268 A1 | 10/2003 | Gerbec et al. | | 2005/0033445 A1 | 2/2005 | Siebel |
| 2003/0204269 A1 | 10/2003 | Gerbec et al. | | 2005/0038443 A1 | 2/2005 | Hedley et al. |
| 2003/0208276 A1 | 11/2003 | Berelsman et al. | | 2005/0043807 A1 | 2/2005 | Wood |
| 2003/0212458 A1 | 11/2003 | Harris et al. | | 2005/0043812 A1 | 2/2005 | Corl et al. |
| 2003/0220697 A1 | 11/2003 | Justin et al. | | 2005/0049524 A1 | 3/2005 | Lefevre et al. |
| 2003/0225457 A1 | 12/2003 | Justin et al. | | 2005/0049713 A1 | 3/2005 | Garber et al. |

| | | |
|---|---|---|
| 2005/0055102 A1 | 3/2005 | Tornier et al. |
| 2005/0059972 A1 | 3/2005 | Biscup |
| 2005/0060040 A1 | 3/2005 | Auxepaules et al. |
| 2005/0071014 A1 | 3/2005 | Barnett et al. |
| 2005/0071015 A1 | 3/2005 | Sekel |
| 2005/0075641 A1 | 4/2005 | Yoon |
| 2005/0080490 A1 | 4/2005 | Bertram |
| 2005/0085823 A1 | 4/2005 | Murphy |
| 2005/0090903 A1 | 4/2005 | Khandkar et al. |
| 2005/0102032 A1 | 5/2005 | Beynnon et al. |
| 2005/0102033 A1 | 5/2005 | Lambert et al. |
| 2005/0102034 A1 | 5/2005 | Hayes et al. |
| 2005/0102038 A1 | 5/2005 | Grundei |
| 2005/0107884 A1 | 5/2005 | Johnson et al. |
| 2005/0119755 A1 | 6/2005 | Kristensen |
| 2005/0125067 A1 | 6/2005 | Sweeney |
| 2005/0131540 A1 | 6/2005 | Trieu |
| 2005/0137603 A1 | 6/2005 | Belew et al. |
| 2005/0137708 A1 | 6/2005 | Clark |
| 2005/0137711 A1 | 6/2005 | Southworth et al. |
| 2005/0143828 A1 | 6/2005 | Collins et al. |
| 2005/0143835 A1 | 6/2005 | Gilbertson |
| 2005/0143836 A1 | 6/2005 | Steinberg |
| 2005/0149043 A1 | 7/2005 | Parry et al. |
| 2005/0149047 A1 | 7/2005 | Parry et al. |
| 2005/0154470 A1 | 7/2005 | Sekel |
| 2005/0154471 A1 | 7/2005 | Aram et al. |
| 2005/0165490 A1 | 7/2005 | Tornier |
| 2005/0165491 A1 | 7/2005 | Diaz |
| 2005/0165492 A1 | 7/2005 | Fitz |
| 2005/0171612 A1 | 8/2005 | Rolston |
| 2005/0177172 A1 | 8/2005 | Acker et al. |
| 2005/0177242 A1 | 8/2005 | Lotke |
| 2005/0177244 A1 | 8/2005 | Steinberg |
| 2005/0187635 A1 | 8/2005 | Metzger |
| 2005/0187637 A1 | 8/2005 | Karrer et al. |
| 2005/0192675 A1 | 9/2005 | Robinson |
| 2005/0202371 A1 | 9/2005 | McGuire |
| 2005/0203535 A1 | 9/2005 | Parry et al. |
| 2005/0203629 A1 | 9/2005 | Cipolletti et al. |
| 2005/0209604 A1 | 9/2005 | Penenberg et al. |
| 2005/0211562 A1 | 9/2005 | Rowe et al. |
| 2005/0216091 A1 | 9/2005 | Wasielewski |
| 2005/0228394 A1 | 10/2005 | Bihary et al. |
| 2005/0228395 A1 | 10/2005 | Auxepaules et al. |
| 2005/0228502 A1 | 10/2005 | Deloge et al. |
| 2005/0228503 A1 | 10/2005 | Gundolf |
| 2005/0240275 A1 | 10/2005 | Chappuis |
| 2005/0240276 A1 | 10/2005 | Shea et al. |
| 2005/0246026 A1 | 11/2005 | Lewis et al. |
| 2005/0246027 A1 | 11/2005 | Metzger et al. |
| 2005/0246028 A1 | 11/2005 | Pappas et al. |
| 2005/0246030 A1 | 11/2005 | Yao |
| 2005/0256576 A1 | 11/2005 | Moskowitz et al. |
| 2005/0256584 A1 | 11/2005 | Farrar |
| 2005/0261776 A1 | 11/2005 | Taylor |
| 2005/0267584 A1 | 12/2005 | Burdulis et al. |
| 2005/0267585 A1 | 12/2005 | Sidebotham |
| 2005/0267590 A1 | 12/2005 | Lee |
| 2005/0278034 A1 | 12/2005 | Johnson et al. |
| 2005/0283252 A1 | 12/2005 | Coon et al. |
| 2005/0283253 A1 | 12/2005 | Coon et al. |
| 2005/0283254 A1 | 12/2005 | Hayes et al. |
| 2005/0288791 A1 | 12/2005 | Tornier et al. |
| 2005/0288793 A1 | 12/2005 | Dong et al. |
| 2006/0004463 A1 | 1/2006 | Lewis et al. |
| 2006/0009774 A1 | 1/2006 | Goble et al. |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0009857 A1 | 1/2006 | Gibbs et al. |
| 2006/0015188 A1 | 1/2006 | Grimes |
| 2006/0030945 A1 | 2/2006 | Wright |
| 2006/0052876 A1 | 3/2006 | Wozencroft et al. |
| 2006/0058883 A1 | 3/2006 | Aram et al. |
| 2006/0058884 A1 | 3/2006 | Aram et al. |
| 2006/0058886 A1 | 3/2006 | Wozencroft |
| 2006/0064169 A1 | 3/2006 | Ferree |
| 2006/0074491 A1 | 4/2006 | Smith et al. |
| 2006/0085079 A1 | 4/2006 | Carroll |
| 2006/0100714 A1 | 5/2006 | Ensign |
| 2006/0129247 A1 | 6/2006 | Brown et al. |
| 2006/0142865 A1 | 6/2006 | Hyde |
| 2006/0142867 A1 | 6/2006 | Metzger et al. |
| 2006/0149285 A1 | 7/2006 | Burgi et al. |
| 2006/0167462 A1 | 7/2006 | Raugel et al. |
| 2006/0167554 A1 | 7/2006 | Heck et al. |
| 2006/0167556 A1 | 7/2006 | Lazennec et al. |
| 2006/0167557 A1 | 7/2006 | Terrill |
| 2006/0167559 A1 | 7/2006 | Johnstone et al. |
| 2006/0167560 A1 | 7/2006 | Heck et al. |
| 2006/0173547 A1 | 8/2006 | Ensign |
| 2006/0173548 A1 | 8/2006 | Auxepaules et al. |
| 2006/0178749 A1 | 8/2006 | Pendleton et al. |
| 2006/0178750 A1 | 8/2006 | Chieng |
| 2006/0184249 A1 | 8/2006 | Tarabishy |
| 2006/0190086 A1 | 8/2006 | Clemow et al. |
| 2006/0206210 A1 | 9/2006 | Abicht et al. |
| 2006/0229734 A1 | 10/2006 | Yoon |
| 2006/0235538 A1 | 10/2006 | Rochetin et al. |
| 2006/0265079 A1 | 11/2006 | D'Alessio |
| 2007/0010890 A1 | 1/2007 | Collazo |
| 2007/0021838 A1 | 1/2007 | Dugas et al. |
| 2007/0088443 A1 | 4/2007 | Hanssen et al. |

FOREIGN PATENT DOCUMENTS

| | | | |
|---|---|---|---|
| EP | 0378928 | | 7/1990 |
| EP | 853930 | | 7/1998 |
| EP | 0947181 | * | 10/1999 |
| EP | 993813 | | 4/2000 |
| FR | 2718953 | | 10/1995 |
| FR | 2793677 A1 | * | 11/2000 |
| JP | 58141847 | | 8/1983 |
| WO | WO-0038598 | | 7/2000 |
| WO | WO-0205732 | | 1/2002 |
| WO | WO-03065939 | * | 8/2003 |
| WO | WO-2004080340 | | 9/2004 |

OTHER PUBLICATIONS

International Search Report and Written Opinion for PCT/US2008/000374 mailed Jun. 6, 2008.*

* cited by examiner

KNEE JOINT PROSTHESIS

CROSS-REFERENCE TO RELATED APPLICATIONS

This is a divisional of U.S. patent application Ser. No. 10/289,585 filed on Nov. 7, 2002, now issued as U.S. Pat. No. 7,025,788, which is a continuation-in-part application of U.S. patent application Ser. No. 09/792,172, filed Feb. 23, 2001, now abandoned. Each of these disclosures is incorporated herein by reference.

FIELD

The present teachings relate generally to a joint prosthesis and more particularly to a knee joint prosthesis having a modular tibial component with an offset tibial stem.

BACKGROUND

A knee joint prosthesis typically comprises a femoral component and a tibial component. The femoral component and tibial component are designed to be surgically attached to the distal end of the femur and the proximal end of the tibia respectively. The femoral component is further designed to cooperate with the tibial component in simulating the articulating motion of an anatomical knee joint. Knee joint prostheses, in combination with ligaments and muscles, attempt to duplicate natural knee motion as well as absorb and control forces generated during the range of flexion.

While known knee joint prostheses have proven to be effective in replacing the anatomical knee joint, they nevertheless have several disadvantages. For example, knee joint prostheses sometimes lack interchangeability between a femoral component designed specifically for a right knee or a left knee and a particular component. In this regard, in a normally shaped tibia, the central canal is typically offset from the center of the tibial articulating surfaces or the center of the tibial plateau. The stems of most prior tibial implants have been positioned centrally to the implant base or tibial tray. Although a central location of the stem allows for particular implant to be used for either the right or left knee, such a stem position is associated with drawbacks. The primary drawback is that the centrally located stem was substantially offset from the center of the tibial canal itself when the base of the implant was aligned with the resected tibial surface.

To a more limited extent, it is also known to provide a knee joint prosthesis with an offset tibia stem. While knee joint prosthesis with offset tibial stems provide certain identified advantages, they nevertheless can be the subject of certain improvement.

SUMMARY

The present teachings relate to a tibial component for a knee joint prosthesis having an offset stem.

A tibial component of a knee joint prosthesis having a common tibial tray and a plurality of tibial stems with various offsets for selectively engaging the tibial tray is disclosed.

A tibial component of a knee joint prosthesis having a offset modular stem that securely engages a tibial tray is disclosed.

A modular component of a knee joint prosthesis that permits different degrees of stem offset with minimal inventory is disclosed.

A tibial component of a knee joint prosthesis having a stem which is offset immediately below a tibial tray is disclosed.

A modular tibial component of a knee joint prosthesis having a stem that easily and securely engages a tray is disclosed.

A modular tibial component of a knee joint prosthesis which provides an offset in any direction within the transverse plane is disclosed.

A modular tibial component for a knee joint prosthesis is disclosed. The modular tibial component includes a tray, a stem and an adapter assembly. The tray includes a support surface and downwardly extending extension having a generally circular shape. The stem includes a main body portion and an upwardly extending extension. The adapter assembly connects the tray and the stem. The adapter assembly includes a first generally cylindrical cavity receiving the downwardly extending extension of the tray and a second generally cylindrical cavity receiving the upwardly extending extension of the stem.

Additional advantages and features will become apparent from the following description and appended claims, taken in conjunction with the accompanying drawings.

BRIEF DESCRIPTION OF THE DRAWINGS

One may more fully understand the detailed description with the accompanying drawings, wherein.

DETAILED DESCRIPTION OF VARIOUS EMBODIMENTS

Figure 1:
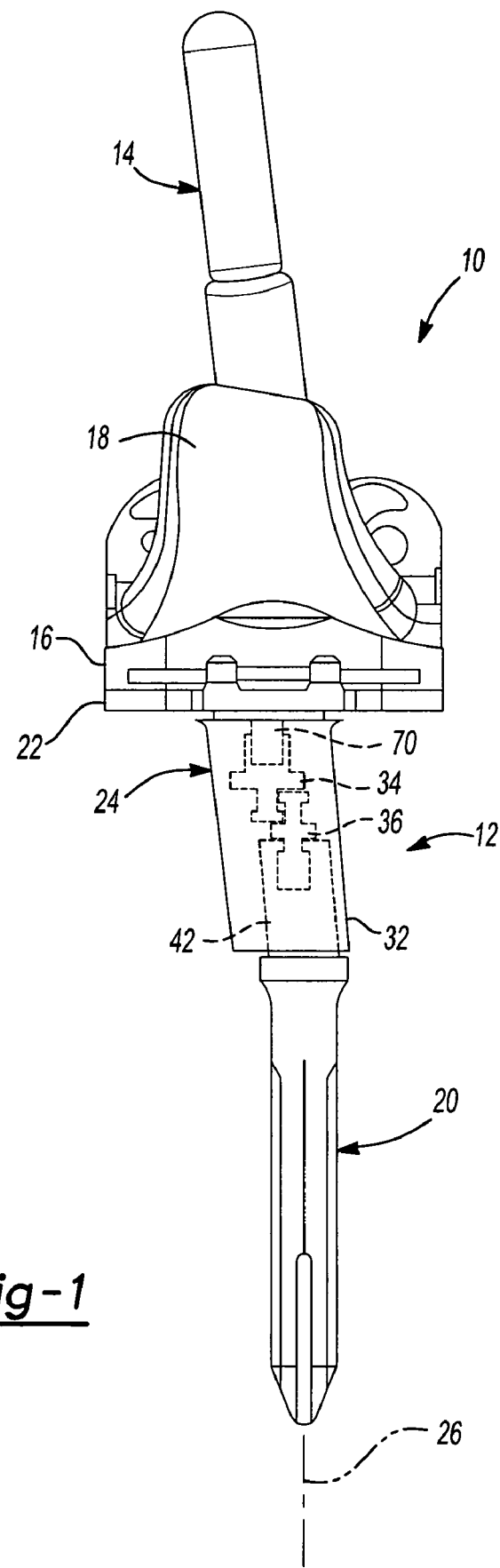
FIG. 1 is a front view illustration of a knee joint prosthesis, the knee joint prosthesis illustrated to include a first adapter assembly for providing a first predetermined offset according to the teachings of a preferred embodiment of the present invention.

With initial reference to FIG. 1, a knee joint prosthesis constructed in accordance with the teachings of a preferred embodiment of the present invention is illustrated and generally identified at reference number 10. The knee joint prosthesis 10 is generally shown to include a tibial component 12 and a femoral component 14. The tibial component 12 supports a bearing 16 which engages an articulation surface 18 of the femoral component 14. Insofar as the present invention is concerned, it will be understood that the femoral component 14 and the bearing 16 shown in FIG. 1 are conventional in construction.

The tibial component 12 illustrated in FIG. 1 will be understood to be modular in construction and generally include a stem 20, a tray 22, and a first adapter assembly 24. In a manner which will be discussed more fully below, the adapter assembly 24 connects the tray 22 and the stem 20 so as to provide an offset to the stem 20 in the transverse plane. Explaining further, when the stem 20 is attached to the tray 22 through the first adapter assembly 24, a central axis of the stem 20 is offset from a central axis 27 of a downwardly extending extension 30 of the tray 22. In the embodiment illustrated, the first adapter assembly 24 provides a first offset of approximately 5 mm. It will become apparent below that the offset can be in any direction in the transverse plane.

Figure 2:
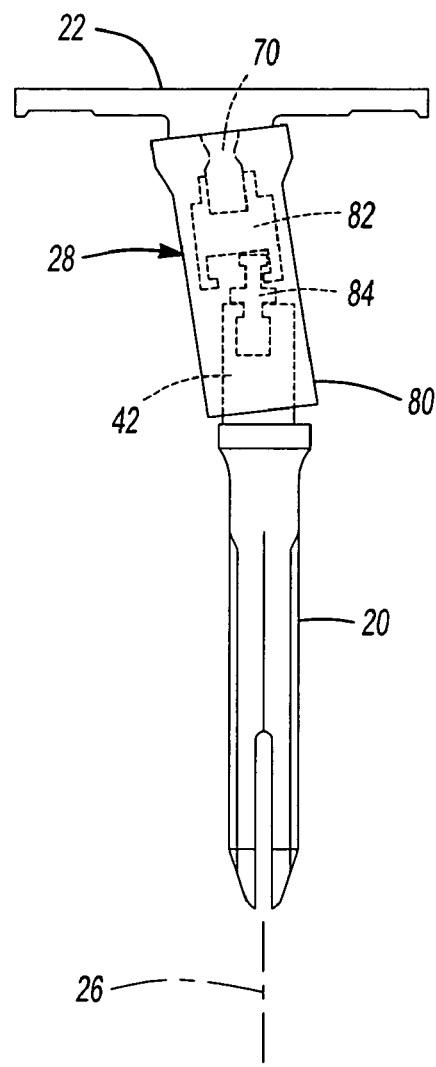
FIG. 2 is front view of a modular tibial component for a knee joint prosthesis including a second adapter assembly according to the teachings of the present invention for providing a second predetermined offset.
Figure 3:
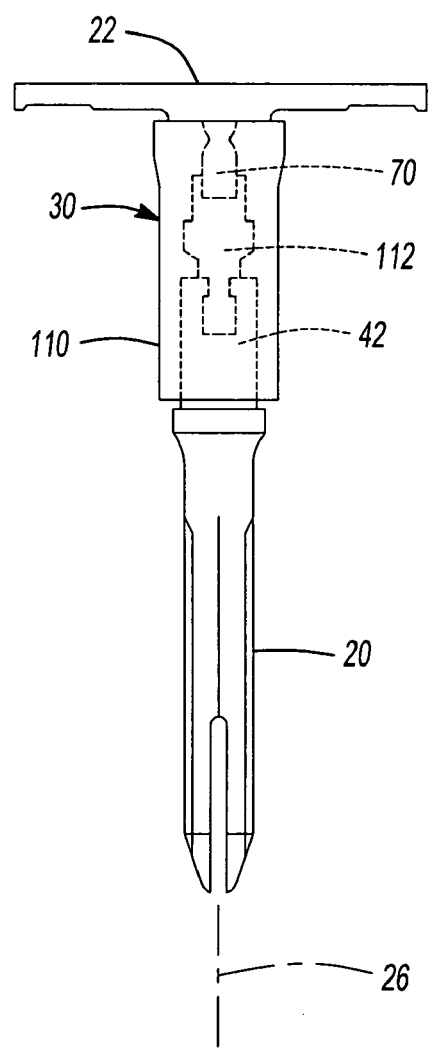
FIG. 3 is front view of a modular tibial component for a knee joint prosthesis including a third adapter assembly according to the teachings of the present invention which does not include an offset.
Figure 4:
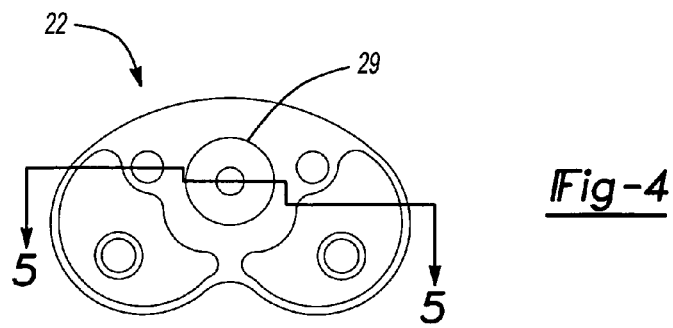
FIG. 4 is a bottom view of the tibial tray of the knee joint prosthesis of FIG. 1.
Figure 5:
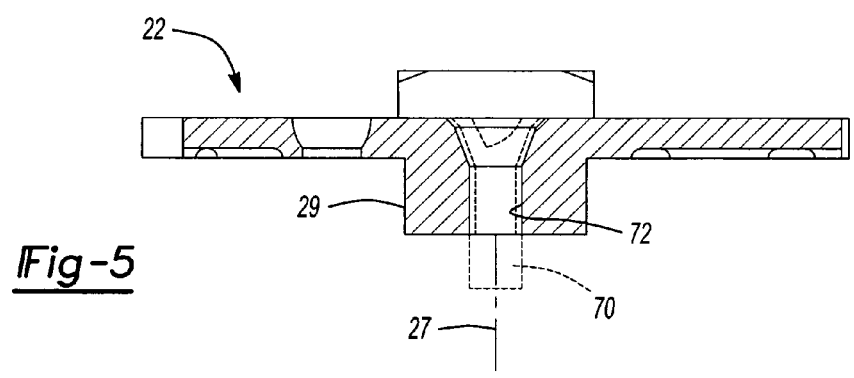
FIG. 5 is a cross-sectional view taken along the line 5-5 of FIG. 4.
Figure 6:
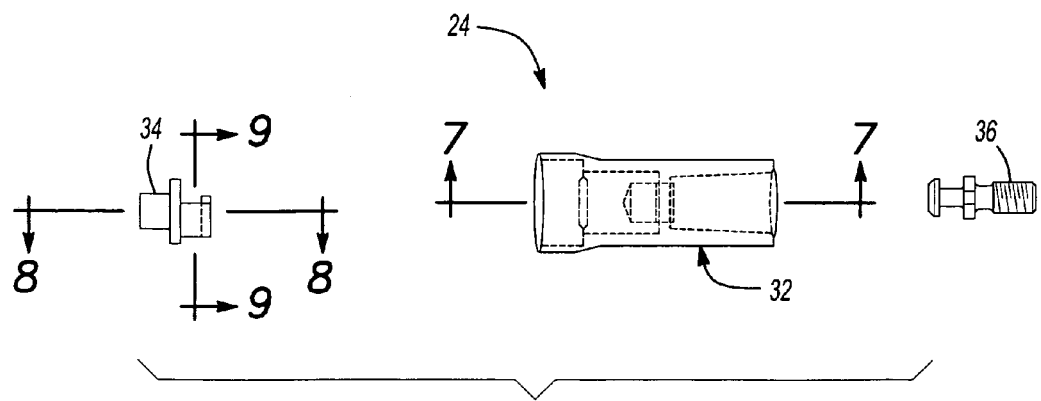
FIG. 6 is an exploded view of a portion of the modular tibial component of FIG. 1.
Figure 7:
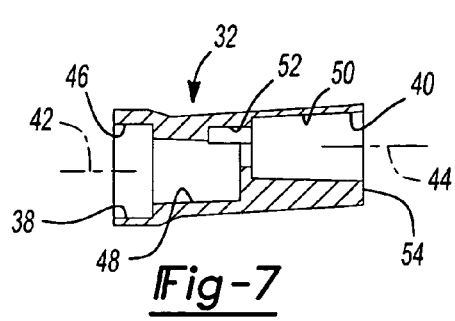
FIG. 7 is a cross-sectional view taken along the line 7-7 of FIG. 6.

With brief reference to FIGS. 2 and 3, second and third adapter assemblies 28 and 30 according to the teachings of the preferred embodiment of the present invention are illustrated, respectively. The second and third adapter assemblies 28 and 30 are shown connecting the tray 22 and stem 20 of FIG. 1. As will be discussed more fully below, the second adapter assembly 28 provides a second offset which in the embodiment illustrated is approximately 2.5 mm. The third adapter assembly is a neutral adapter assembly 30 and does not provide any offset. Explaining further, the central axis 26 of the stem 20 is aligned with the central axis 27 of the downwardly extending extension 29 of the tray 22. It will be appreciated by those skilled in the art that the particular degrees of offset provided by the various adapter assemblies 24, 28, and 30 of the present invention are strictly a matter of design choice. Alternate offsets will be understood to fall within the scope of the present invention.

With continued reference to FIG. 1 and additional reference to FIGS. 4 through 10, the first adapter assembly 24 will be further described. The first adapter assembly 24 is illustrated to generally include an adapter body 32, a locking insert member 34 and a stem insert member 36. The adapter body 32 of the first adapter assembly 24 is shown to include a first generally cylindrical cavity 38 for receiving the downwardly extending extension 29 of the tray 22 and a second generally cylindrical cavity 40 for receiving and upwardly extending extension 42 of the stem 20. The first generally cylindrical cavity 38 includes a first central axis 42 and the second generally cylindrical cavity 40 includes a second generally cylindrical axis 44. In the embodiment illustrated, the first central axis 42 and the second central axis 44 are parallel to one another and spaced apart. Insofar as the first adapter assembly 24 provides a 5 mm offset, the first and second central axes 42 and 44 are spaced apart 5 mm.

The first generally cylindrical cavity 38 includes a first portion 46 for directly receiving the downwardly extending extension 29 of the tray 22 and a second reduced diameter portion 48 which receives the locking insert 34. The first portion 46 preferably tapers slightly as it extends into the adapter body 32 from a top end of the adapter body 32. The second generally cylindrical cavity 40 similarly includes a first portion 50 and a second portion 52 of reduced diameter. The first portion 50 preferably tapers slightly as it extends into the adapter body 32 from a lower end 54 of the adapter body 32. The second portion 52 of the second generally cylindrical cavity 40 is shown to intersect the second portion 48 of the first generally cylindrical cavity 38. In a manner to be described further below, the stem insert 36 is partially disposed within the first portion 50 and extends into the second portion 52 where it engages the locking insert member 34.

Figure 10:
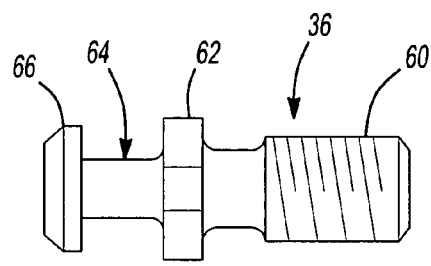
FIG. 10 is an enlarged view of the stem insert according to the present invention and shown in FIG. 6.
Figure 11:
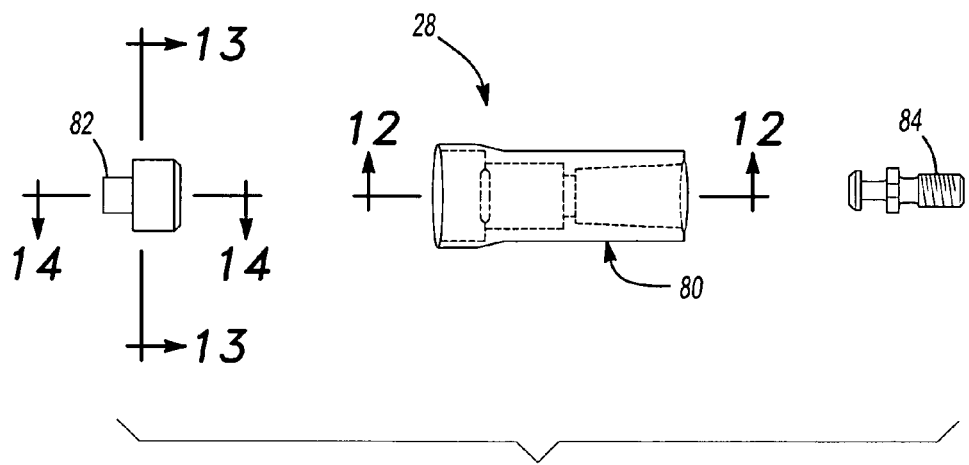
FIG. 11 is an exploded view similar to FIG. 6, illustrating a portion of the modular tibial component of FIG. 2.
Figure 12:
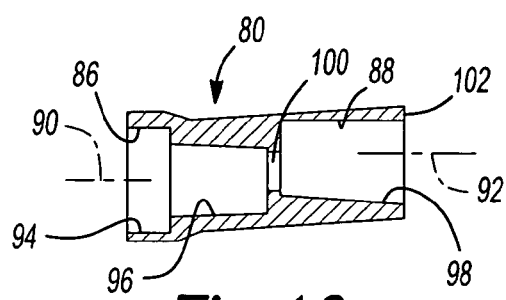
FIG. 12 is a cross-sectional view taken along the line 12-12 of FIG. 11.

With particular reference to FIG. 10, the stem insert member 36 is illustrated to include a lower portion 60 which is externally threaded for engaging an internally threaded aperture of the upwardly extending extension 42 of the stem 20. The stem insert member 36 further includes a central portion 62 having a hexagonal or other suitable cross-section which can be engaged by a tool (not shown) for rotating the stem insert member 36 into the stem 20. Further, the stem insert member 36 includes an upper end 64 including an enlarged diameter head 66 which extends into the second portion 52 of the second generally cylindrical cavity 40.

Figure 8:
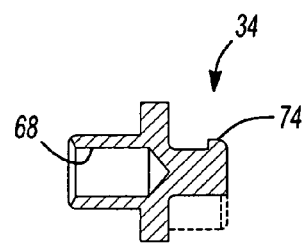
FIG. 8 is a cross-sectional view taken along the line 8-8 of FIG. 6.
Figure 9:
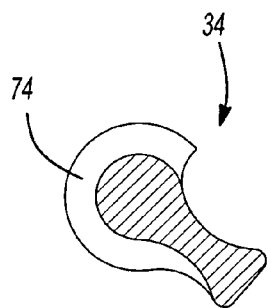
FIG. 9 is a cross-sectional view taken along the line 9-9 of FIG. 6.

With particular reference to the cross-sectional views of FIGS. 8 and 9, the locking insert member 34 will be further described. The locking insert member 34 includes an upper portion having an internally threaded aperture 68 and having a square, hexagonal or other suitable cross section that can be engaged by a tool (not shown). The internally threaded aperture 68 threadably receives a fastener 70 which extends through a central aperture 72 provided in the tray 22. The locking insert member 34 additionally includes a radially extending segment 74 for engaging the head 66 of the stem insert member 36.

Upon selection by the surgeon of the first adapter assembly 24, the stem insert member 36 is screwed into the stem 20. Next, the adapter body 32 is placed over the upwardly extending extension 42 of the stem 20 such that the upwardly extending portion 42 is received in a press fit within the first portion 50 of the first generally cylindrical aperture 40 and the upper end 64 of the stem insert member 36 extends into the reduced diameter second portion 52 of the second generally cylindrical cavity 40. At this point, the locking insert member 34 is inserted into the first generally cylindrical cavity 38 with the radially extending segment 74 opposite the side of the reduced diameter portion 48 which intersects the reduced diameter portion 52. Upon complete insertion, the locking insert member 34 is rotated approximately between 180° and 270° such that the radially extending portion 74 engages the enlarged head 66 of the stem insert member 36.

The adapter body 32 is rotated about the axis 27 to provide the offset in the desired direction. The first portion 46 of the first generally cylindrical cavity 38 is now press fit onto the downwardly extending extension 29 of the tray 22. The stem 20 is secured to the tray 22 by the threaded fastener 70 which extends through the aperture 72 and threadably engages the internally threaded aperture 68 of the locking insert member 34. Rotation of the threaded fastener 70 in a clockwise direction causes the locking insert member 34 to be drawn towards the tray 22 and a secure connection to be established between the tray 22 and the stem 20.

With reference now to FIGS. 2 and 11 through 14, the second adapter assembly 28 of the present invention will now be described. The second adapter assembly 28 is illustrated to generally include an adapter body 80, a locking insert member 82 and a stem insert member 84. The stem insert member 84 is identical to stem insert member 36 described above.

The adapter body 80 of the second adapter assembly 28 is shown to include a first generally cylindrical cavity 86 for receiving the downwardly extending extension 29 of the tray 22 and a second generally cylindrical cavity 88 for receiving the upwardly extending extension 42 of the stem 20. The first generally cylindrical cavity 86 includes a first central axis 90 and the second generally cylindrical cavity 88 includes a second generally cylindrical axis 92. In the embodiment illustrated, the first central axis 90 and the second central axis 92 are parallel to one another and spaced apart. Insofar as the second adapter assembly 80 provides a 2.5 mm offset, the first and second central axes 90 and 92 are spaced apart 2.5 mm.

The first generally cylindrical cavity 86 includes a first portion 94 for directly receiving the downwardly extending extension 29 of the tray 22 and a second reduced diameter portion 96 which receives the locking insert 82. As with the first adapter assembly 24, the first portion 94 preferably tapers slightly as it extends into the adapter body 80 from a top end. The second generally cylindrical cavity 88 similarly includes a first portion 98 and a second portion 100 of reduced diameter. The first portion 98 preferably tapers slightly as it extends into the adapter body 80 from a lower end 102 of the adapter body 80. The second portion 100 of the second generally cylindrical cavity 88 is shown to intersect the second portion 96 of the first generally cylindrical cavity 86.

Figure 14:
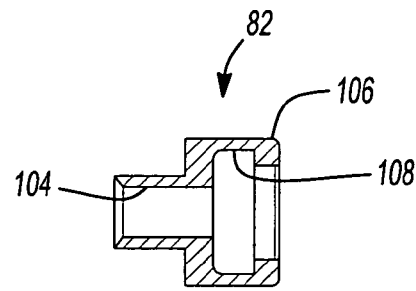
FIG. 14 is a cross-sectional view taken along the line 14-14 of FIG. 11.
Figure 13:
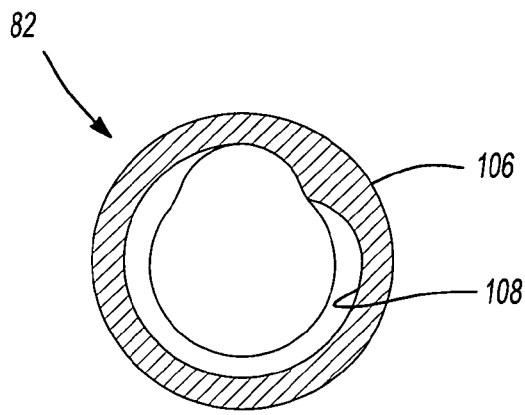
FIG. 13 is a cross-sectional view taken along the line 13-13 of FIG. 11.
Figure 16:
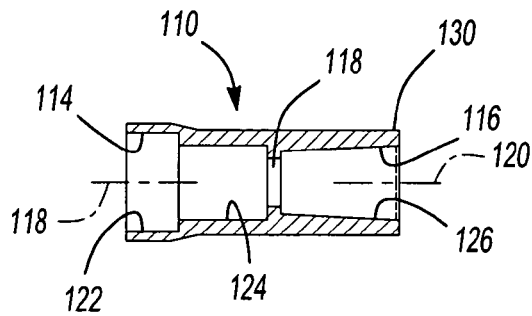
FIG. 16 is a cross-sectional view taken along the line 16-16 of FIG. 15.

With particular reference to the cross-sectional views of FIGS. 13 and 14, the locking insert member 82 will be further described. The locking insert member 82 includes an upper portion having an internally threaded aperture 104 and having a square, hexagonal or other suitable cross section that can be engaged by a tool. The internally threaded aperture 104 threadably receives the fastener 70 which extends through the central aperture 72 in the tray 22. The locking insert member 82 additionally includes a radially extending segment 106 defining a cavity 108 for engaging the head 66 of the stem insert member 36. The aperture 108 includes a non-cylindrical opening for receiving the head 66 of the stem insert member 36 and retaining the head 66 upon rotation in the manner discussed above with respect to the first adapter assembly 24.

With reference now to FIGS. 3 and 15 through 17, the third adapter assembly 30 of the present invention will now be described. The third adapter assembly 30 is illustrated to generally include an adapter body 110 and a locking insert member 112. The adapter body 110 of the third adapter assembly 30 is shown to include a first generally cylindrical cavity 114 for receiving the downwardly extending extension 29 of the tray 22 an a second generally cylindrical cavity 116 for receiving the upwardly extending extension 42 of the stem 20. The first generally cylindrical cavity includes a first central axis 118 and the second generally cylindrical cavity includes a second generally cylindrical axis 120. In the embodiment illustrated, the first central axis 118 and the second central axis 120 are coincident as the third adapter assembly 30 does not provide any offset.

The first generally cylindrical cavity 114 includes a first portion 122 for directly receiving the downwardly extending extension 29 of the tray 22 and a second reduced diameter portion 124 which receives the locking insert 112. The first portion 122 preferably tapers slightly as it extends into the adapter body 110 from an upper end. The second generally cylindrical cavity 116 similarly includes a first portion 126 and a second portion 128 of reduced diameter. The first portion 126 preferably tapers slightly as it extends into the adapter body 110 from a lower end 130 of the adapter body 110. The second portion 128 of the second generally cylindrical cavity 126 is shown to communicate with the second portion 124 of the first generally cylindrical cavity 114.

Figure 17:
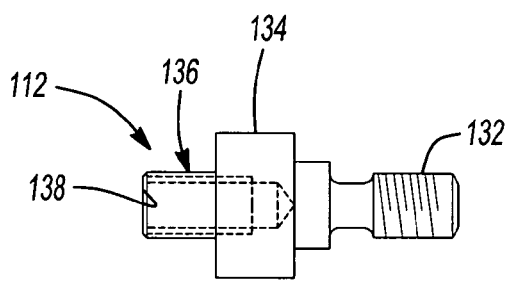
FIG. 17 is an enlarged view of the locking insert of FIG. 15.
Figure 15:
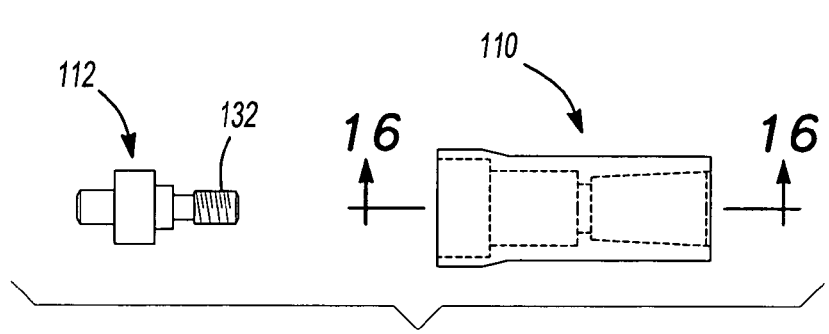
FIG. 15 is another exploded view similar to FIG. 6, illustrating a portion of the modular tibial component of FIG. 3.

With particular reference to FIG. 17, the locking insert member 112 is illustrated to include a lower portion 132 which is externally threaded for engaging the internally threaded aperture of the upwardly extending extension 42 of the stem 20. The locking insert member 112 further includes a central portion 134 and an upper portion 136. The upper portion has a square, hexagonal or other suitable cross section which can be engaged by a tool (not shown) for rotating the locking insert member 112 into the stem 20. The internally threaded aperture 138 threadably receives the fastener 70 which extends through the central aperture 72 provided in the tray 22.

Figure 18:
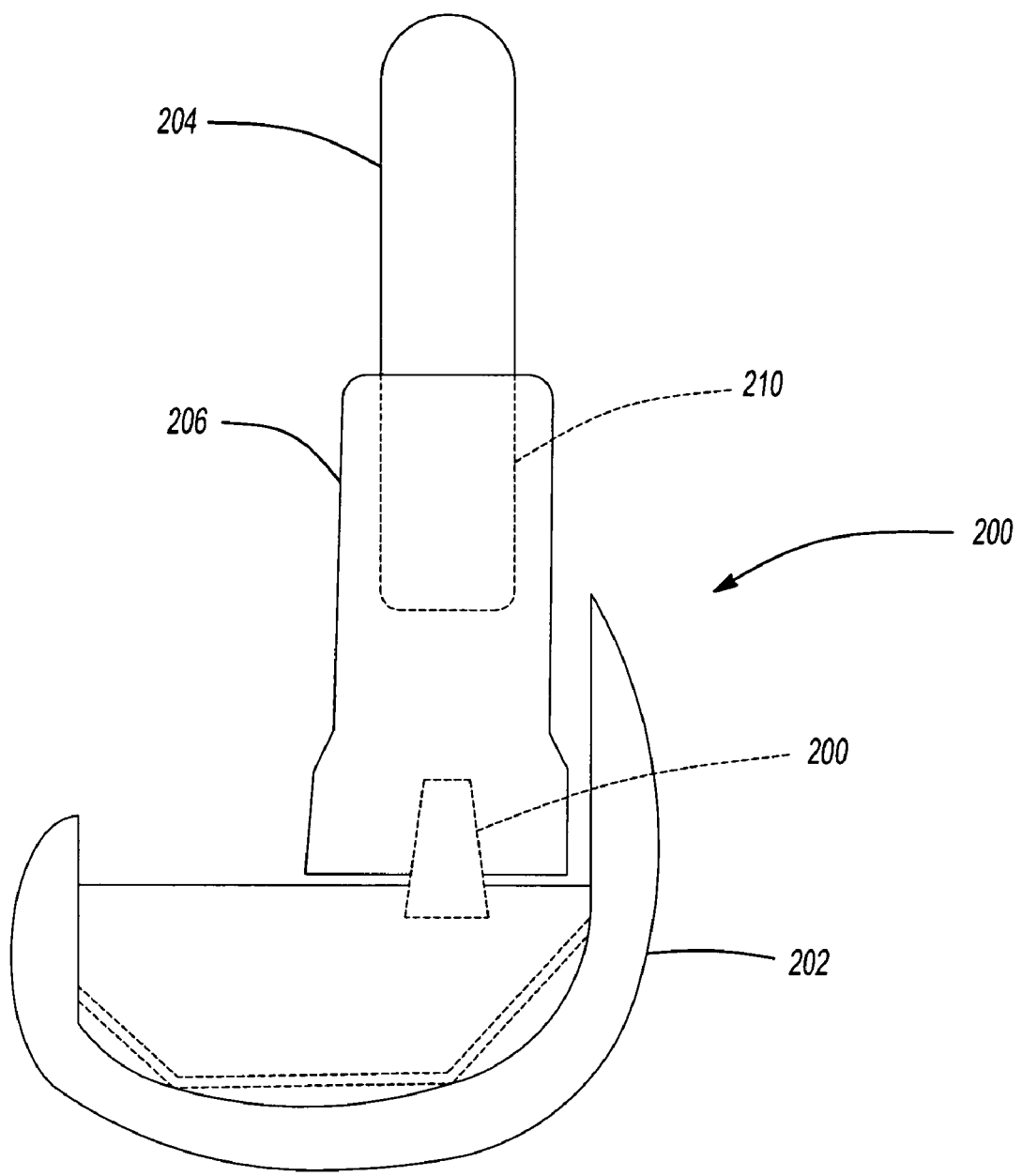
FIG. 18 is an illustration of a modular femoral component for a knee joint prosthesis according to the teachings of the present invention.

Turning to FIG. 18, a modular femoral component for a knee joint prosthesis of the present invention is generally identified at reference 200. The embodiment of FIG. 18 illustrates application of the teachings of the first preferred embodiment of the present invention adapted to a modular femoral component 200. The modular femoral component 200 includes an articulating member 202, a stem 204 and an adapter assembly 206. While not shown in great detail, it will be understood by those skilled in the art that the adapter assembly 206 is substantially identical to the first adapter assembly 24 described above. In this regard, the adapter assembly 206 connects the articulating member 202 and the stem 204 and provides an offset between an upwardly extending extension 208 of the articulating member and a downwardly extension 210 of the stem 204. The adapter assembly 206 will be understood to include an adapter body, locking insert member and stem insert member substantially identical to that described above with respect to the first adapter assembly 24. Alternatively, it will be understood that the adapter assembly of the modular femoral component 200 may be similar to either of the second and third adapter assemblies 28 and 30.

With reference to FIGS. 19, 20 and 21A through 21C, a tibial component for a knee joint prosthesis constructed in accordance with the teachings of a second preferred embodiment of the present invention is illustrated and generally identified at reference number 302. It will be understood that the knee joint prosthesis further includes a femoral component that cooperates with the tibial component 302. The particular construction of the femoral component is beyond the scope of the subject invention. One suitable femoral component is, however, shown in connection with the first preferred embodiment.

The tibial component 302 of the second preferred embodiment of the present invention will be understood to be modular in construction and generally include a stem 304, a tray 306, and an adapter assembly 308. In a manner which will be discussed more fully below, the adapter assembly 308 connects the tray 306 and the stem 304 so as to provide an offset to the stem 304 in the transverse plane. Explaining further, when the stem 304 is attached to the tray 306 through the adapter assembly 308, a central axis of the stem 304 is offset from a central axis of a downwardly extending extension 310 of the tray 306. In the embodiment illustrated, the adapter assembly 308 provides an offset of approximately 5 mm. As with the first preferred embodiment, the offset provided by the adapter assembly 308 preferably ranges from 0 mm to approximately 5 mm or more and can be in any direction in the transverse plane.

The adapter assembly 308 is illustrated to generally include an adapter body 312 and a locking member or element 314. The adapter body 312 of the adapter assembly 308 is shown to define a first cavity 316 for receiving the downwardly extending extension 310 of the tray 306 and a second cavity 318 for receiving and upwardly extending extension 320 of the stem 304. In the preferred embodiment, the first and second cavities 316 and 318 are generally cylindrical. The first cavity 316 includes a first central axis and the second cavity 318 includes a second cylindrical axis. Further, in the embodiment illustrated, the first central axis and the second central axis are parallel to one another and spaced apart. Insofar as the adapter assembly 308 provides a 5 mm offset, the first and second central axes are spaced apart 5 mm.

The first cavity 316 tapers slightly as it extends into the adapter body 312 from a top end 326 of the adapter body 312. The second cavity 318 similarly tapers slightly as it extends into the adapter body 312 from a lower end 322 of the adapter body 312. The adapter body 312 is illustrated to further define a laterally extending channel 324 which intersects both the first cavity 316 and the second cavity 318. In a manner to be described further below, the locking element 314 extends into the laterally extending channel 324 where it couples the tray 306 to the stem 304.

Figure 19:
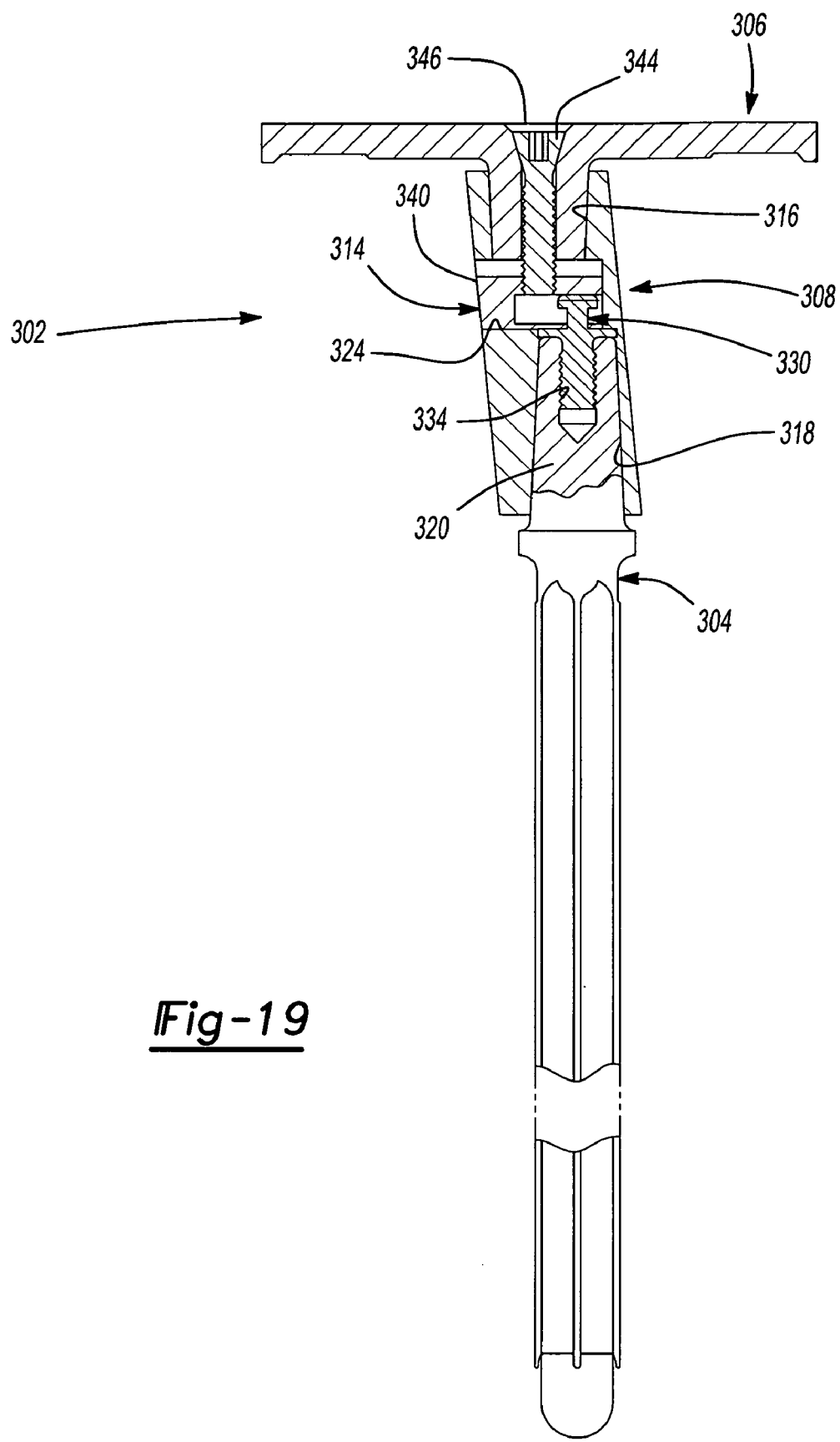
FIG. 19 is a front view illustration of a knee joint prosthesis constructed in accordance with the teachings of a second preferred embodiment of the present invention.
Figure 20:
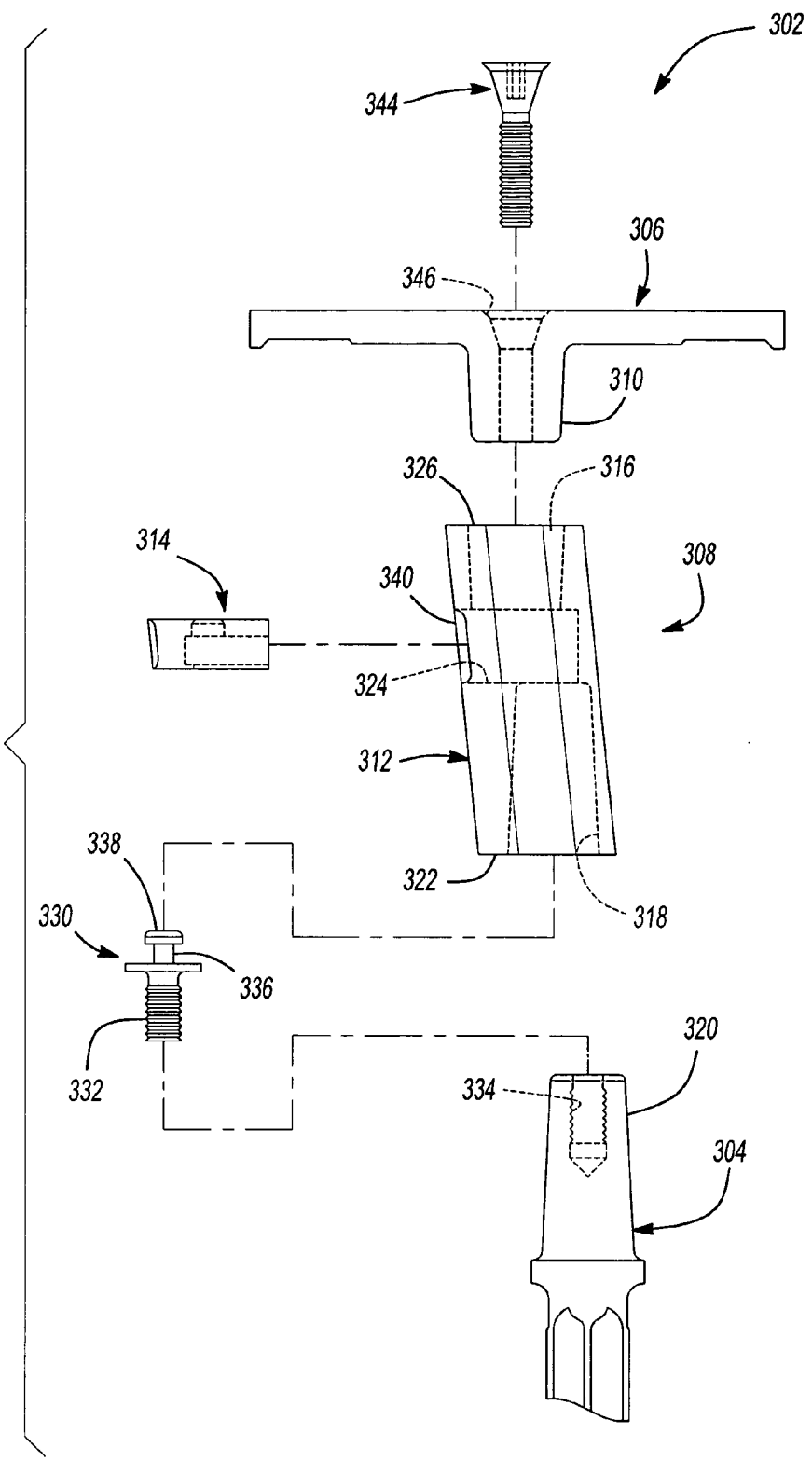
FIG. 20 is an exploded view of the knee joint prosthesis of FIG. 19.
Figure 21A:
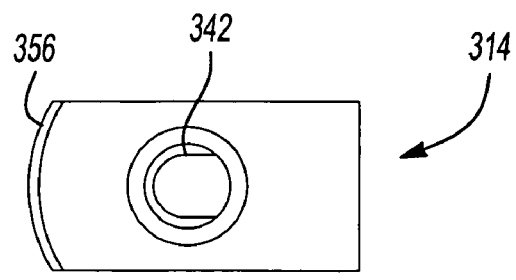
FIGS. 21A-21C are top, side and bottom views, respectively, of the locking element of the knee joint prosthesis of FIG. 19.
Figure 21B:
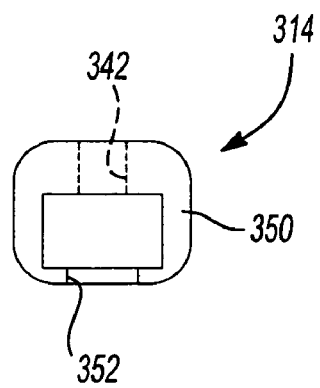
Figure 21C:
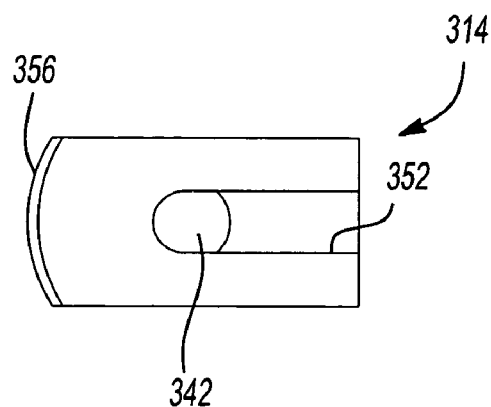

As shown in FIGS. 19 and 20, the stem 304 is illustrated to include an upper portion that cooperatively engages with the locking element 314. In the embodiment illustrated, the upper portion of the stem 304 includes a stem insert member. Alternatively, the upper portion of the stem 304 may be integrally formed to cooperate with the locking element 314.

The stem insert member 330 is illustrated to include a lower portion 332 which is externally threaded for engaging an internally threaded aperture 334 of the upwardly extending extension 320 of the stem 304. The stem insert member 330 further includes a central portion 336 having a hexagonal or other suitable cross-section which can be engaged by a tool (not shown) for rotating the stem insert member 330 into the stem 304. Further, the stem insert member 330 includes an upper end including an enlarged diameter head 338.

The locking element 314 is sized and configured to be inserted through an opening 340 in the sidewall of the adapter body 312 and into the channel 324 for coupling of the stem 304 and the tray 306. The locking element 314 includes an upper surface (see FIG. 19) having an internally threaded aperture 342. The internally threaded aperture 342 threadably receives a fastener 344 which extends through a central aperture 346 provided in the tray 306. The fastener 344 is aligned with the central longitudinal axis of the downwardly extending portion 310 of the tray 306.

The locking element 314 is illustrated to additionally include an open end 350 and a bottom surface having a slot 352. The slot 352 intersects the open end 350. The open end 350 receives the head 338 of the stem insert 330 as the locking element 314 is inserted through the opening 340. The slot 352 accommodates the reduced diameter, central portion 336 of the stem insert 330. The head 338 of the stem insert 330 has a diameter greater than a width of the slot 352 for coupling of the stem insert 330 with the locking element 314.

The locking element 314 further includes a closed end 356. The closed end 356 is preferably convexly curved. When the locking element 314 is completely inserted into the channel 324, the closed end 356 is flush with the sidewall of the adapter body 312.

In use, the stem insert member 330 is screwed into the stem 304. Next, the adapter body 312 is placed over the upwardly extending extension 320 of the stem 304 such that the upwardly extending portion 320 is received in a press fit within the second aperture 318 and the upper end of the stem insert member 330 extends into the laterally extending channel 324.

The first cavity 316 is now press fit onto the downwardly extending extension 310 of the tray 306 with the adapter body 312 oriented to provide the offset in the desired direction. At this point, the locking element 314 is inserted into the laterally extending channel 324 through the opening 340. Upon complete insertion, the locking element 314 engages the stem insert member 330. The tray 306 is secured to the adapter body 312 by the threaded fastener 344 which extends through the aperture 346 and threadably engages the internally threaded aperture 342 of the locking element 314.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A modular tibial component for a knee joint prosthesis, the modular tibial component comprising:
    a tibial tray having a support surface and a first extension;
    a tibial stem having a main body portion and a second extension;
    an adapter body extending along a longitudinal axis and connecting the tray and the stem and establishing a non-zero offset between the first extension of the tray and the second extension of the stem, the adapter body defining a first cavity to receive the first extension of the tray and a second cavity to receive the second extension of the stem, the adapter body further including a sidewall defining an opening communicating with a passage, the passage transversely intersecting the longitudinal axis and the first and second cavities; and
    a locking mechanism for coupling the tray to the stem, the locking mechanism including a first locking element passing through the opening into the passage and coupling the first and second extensions.

2. The modular tibial component for a knee joint prosthesis of claim 1, wherein the first cavity is generally cylindrical and includes a first central axis and the second cavity is generally cylindrical and includes a second central axis, the first and second central axes being parallel to one another and spaced apart.

3. The modular tibial component for a knee joint prosthesis of claim 1, wherein the locking element includes an upper surface having an internally threaded aperture, the aperture threadably receiving fastener extending through the first extension of the tray.

4. The modular tibial component for a knee joint prosthesis of claim 1, wherein the locking element includes an open end and a bottom surface having a slot for receiving a portion of the stem as the locking element is inserted through the opening.

5. The modular tibial component for a knee joint prosthesis of claim 4, wherein the portion of the stem received in the slot is an insert threadably coupled with the stem.

6. The modular tibial component for a knee joint prosthesis of claim 1, wherein the stem includes a reduced diameter portion, the locking element engaging the reduced diameter portion.

7. The modular tibial component for a knee joint prosthesis of claim 1, wherein the locking element includes an open end and a bottom surface having a slot intersecting the open end and wherein the stem includes a head received in the open end and having a diameter greater than a width of the slot.

8. The modular tibial component of claim 1,
wherein the locking mechanism includes a second locking element;
wherein the second locking element is operable to pass through at least a portion of one of the first cavity, the second cavity, or combinations thereof to engage the first locking element.

9. The modular tibial component of claim 8, wherein the first locking element is operable to interact with the second locking element to draw the tibial tray toward the second locking element.

10. The modular tibial component of claim 9, wherein the first locking element includes a threaded aperture and the second locking element includes an externally threaded portion threadably engaging the threaded aperture.

11. A modular component for implanting in a portion of an anatomy, comprising:
a tray having a support surface and a first extension;
a stem having a body portion and a second extension;
an adapter extending along a longitudinal axis and operable to connect the tray and the stem, the adapter defining a first cavity to receive the first extension and a second cavity to receive the second extension, the second cavity transversely offset relative to the first cavity by a nonzero offset, the adapter having an outer wall defining a passage transversely intersecting the longitudinal axis and the second cavity;
a stem insert having a head, central portion of reduced width relative to the head, and an end portion coupled to the second extension; and
a locking member received in the passage and lockingly engaging the central portion of the stem insert.

12. The modular component of claim 11, wherein the end portion of the stem insert threadably engages a threaded recess of the second extension.

13. The modular component of claim 11, wherein the locking member includes a slot engaging the central portion of the insert.

* * * * *

UNITED STATES PATENT AND TRADEMARK OFFICE
CERTIFICATE OF CORRECTION

PATENT NO. : 7,445,639 B2 Page 1 of 1
APPLICATION NO. : 11/358926
DATED : November 4, 2008
INVENTOR(S) : Metzger et al.

It is certified that error appears in the above-identified patent and that said Letters Patent is hereby corrected as shown below:

Column 1
Line 60, "having a" should be --having an--.

Column 4
Line 20, insert --member-- after "insert".

Column 8
Line 66, insert --a-- after "receiving".

Signed and Sealed this

Seventeenth Day of March, 2009

JOHN DOLL
*Acting Director of the United States Patent and Trademark Office*